(12) United States Patent
Shudo et al.

(10) Patent No.: US 10,117,569 B2
(45) Date of Patent: Nov. 6, 2018

(54) DIAGNOSIS SUPPORTING DEVICE AND DIAGNOSIS SUPPORTING METHOD

(71) Applicant: JVC KENWOOD CORPORATION, Yokohama-shi (JP)

(72) Inventors: Katsuyuki Shudo, Yokohama (JP); Masaru Ninomiya, Yokohama (JP); Shuji Hakoshima, Yokohama (JP)

(73) Assignee: JVC KENWOOD Corporation, Yokohama-shi (JP)

( * ) Notice: Subject to any disclaimer, the term of this patent is extended or adjusted under 35 U.S.C. 154(b) by 109 days.

(21) Appl. No.: 14/844,934

(22) Filed: Sep. 3, 2015

(65) Prior Publication Data
US 2015/0374223 A1    Dec. 31, 2015

Related U.S. Application Data

(63) Continuation of application No. PCT/JP2014/055522, filed on Mar. 4, 2014.

(30) Foreign Application Priority Data

Mar. 7, 2013  (JP) .................................. 2013-045357
Feb. 20, 2014  (JP) .................................. 2014-031023

(51) Int. Cl.
*A61B 3/14*       (2006.01)
*A61B 3/10*       (2006.01)
(Continued)

(52) U.S. Cl.
CPC .......... *A61B 3/0058* (2013.01); *A61B 3/0025* (2013.01); *A61B 3/113* (2013.01); *A61B 5/168* (2013.01); *A61B 5/4088* (2013.01)

(58) Field of Classification Search
CPC ... A61B 3/0008; A61B 3/0025; A61B 3/0041; A61B 3/0058; A61B 3/0091; A61B 3/11; A61B 3/111; A61B 3/113
(Continued)

(56) References Cited

U.S. PATENT DOCUMENTS 8,339,446 B2 * 12/2012 Blixt ...................... A61B 3/113
                                                            348/78
8,371,693 B2    2/2013 Ebisawa
(Continued)

FOREIGN PATENT DOCUMENTS

JP    2005-185431 A    7/2005
JP    2005-198743 A    7/2005
(Continued)

OTHER PUBLICATIONS

Pierce et al., "Preference for Geometric Patterns Early in Life as a Risk Factor for Autism," Archives of General Psychiatry, vol. 68, No. 1, Jan. 2011, pp. 101-109.
(Continued)

*Primary Examiner* — Dawayne A Pinkney
(74) *Attorney, Agent, or Firm* — Venable LLP; Michael A. Sartori; Laura G. Remus

(57) ABSTRACT

A diagnosis supporting device includes an imaging unit that images a subject, an eye gaze detector that detects an eye gaze direction of the subject from an image captured by the imaging unit, a gaze point detector that detects a gaze point of the subject in a display area of a display on the basis of the eye gaze direction, and an output controller that causes the display area to display a diagnostic image composed by superposing a pattern image onto a natural image.

8 Claims, 22 Drawing Sheets

(51) Int. Cl.
*A61B 3/00* (2006.01)
*A61B 3/113* (2006.01)
*A61B 5/16* (2006.01)
*A61B 5/00* (2006.01)

(58) Field of Classification Search
USPC .................. 351/204, 205, 206, 209, 221
See application file for complete search history.

(56) References Cited

U.S. PATENT DOCUMENTS

| | | | |
|---|---|---|---|
| 9,579,054 B2* | 2/2017 | Shudo | A61B 5/168 |
| 2010/0249532 A1* | 9/2010 | Maddess | A61B 3/024 |
| | | | 600/300 |
| 2012/0154751 A1* | 6/2012 | Pelah | A61B 3/0041 |
| | | | 351/224 |

FOREIGN PATENT DOCUMENTS

| | | |
|---|---|---|
| JP | 2008-125619 A | 6/2008 |
| JP | 2011-206542 A | 10/2011 |

OTHER PUBLICATIONS

Extended European Search Report in counterpart European Patent Application No. 14761135.4, dated Dec. 12, 2016.
Karen Pierce et al., "Preference for Geometric Patterns Early in Life as a Risk Factor for Autism," Arch Gen Psychiatry, vol. 68 (No. 1), pp. 101-109, Jan. 2011.
International Search Report in PCT International Application No. PCT/JP2014/055522 dated Apr. 1, 2014.

* cited by examiner

DIAGNOSIS SUPPORTING DEVICE AND DIAGNOSIS SUPPORTING METHOD

CROSS-REFERENCE TO RELATED APPLICATIONS

This application is a continuation of PCT international application Ser. No. PCT/JP2014/055522 filed on Mar. 4, 2014 which designates the United States, incorporated herein by reference, and which claims the benefit of priority from Japanese Patent Application No. 2013-045357, filed on Mar. 7, 2013 and Japanese Patent Application No. 2014-031023, filed on Feb. 20, 2014, incorporated herein by reference.

BACKGROUND OF THE INVENTION

1. Field of the Invention

The present invention relates to a diagnosis supporting device and a diagnosis supporting method.

2. Description of the Related Art

It is said that the number of people with developmental disorder is on the rise recently. Those with the developmental disorder can more effectively adapt to the society when the symptom is alleviated by early detection and start of rehabilitation. Our country aims at early detection of the disorder as well by an interview or the like performed at the time of an 18-month medical checkup. However, the effect of such effort is not sufficient due to problems such as a shortage of psychiatrists and the time it takes to perform the interview. Therefore, an objective and efficient diagnosis supporting device for the developmental disorder is being required.

It is ideal to be able to perform a diagnosis at the time of the 18-month medical checkup, for example, in order to achieve early detection of the developmental disorder. A characteristic of a child with the developmental disorder is that he does not look a person facing him in the eye (looks away). There is proposed a method that supports diagnosis of the developmental disorder by applying a method that captures a face of a person with a camera, calculates corneal reflection and pupil positions, and detects a gaze point.

A subject who is around 18 months old has a tendency of not gazing at an object that does not move much. Therefore, the conventional method of detecting the gaze point cannot properly support the diagnosis in some cases and thus a more accurate detection method is being required.

Therefore, there is a need for a diagnosis supporting device and a diagnosis supporting method which can improve the diagnostic accuracy.

SUMMARY OF THE INVENTION

It is an object of the present invention to at least partially solve the problems in the conventional technology.

There is provided a diagnosis supporting device that includes an imaging unit which images a subject, an eye gaze detector which detects an eye gaze direction of the subject from an image captured by the imaging unit, a gaze point detector which detects a gaze point of the subject in a display area of a display on the basis of the eye gaze direction, and an output controller that causes the display area to display a diagnostic image composed by superposing a pattern image onto a natural image.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Embodiments of a diagnosis supporting device and a diagnosis supporting method according to the present invention will now be described in detail with reference to the drawings. The present invention is not to be limited by these embodiments.

First Embodiment

Figure 1:
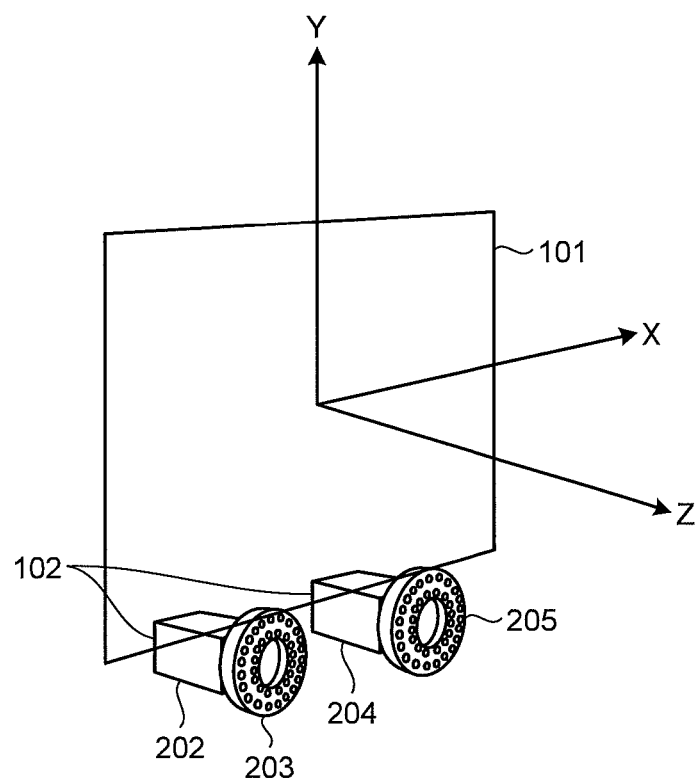
FIG. 1 is a diagram illustrating an example of arrangement of a display, a stereo camera, and a light source used in a first embodiment.

FIG. 1 is a diagram illustrating an example of arrangement of a display, a stereo camera, and a light source used in the first embodiment. In the present embodiment, a pair of stereo cameras 102 is arranged at the bottom of a display screen 101 as illustrated in FIG. 1. The stereo cameras 102 are imaging units capable of performing stereo imaging with infrared ray, and include a right camera 202 and a left camera 204.

Infrared LED (Light Emitting Diode) light sources 203 and 205 are arranged right in front of a lens of each of the right camera 202 and the left camera 204 along a circumferential direction. Each of the infrared LED light sources 203 and 205 includes an inner peripheral LED and an outer peripheral LED, which emits light having different wavelengths from each other. The infrared LED light sources 203 and 205 are used to detect a pupil of a subject. The method disclosed in Patent Literature 2 can be applied as a method of detecting a pupil, for example.

An eye gaze is detected by identifying a position in a space expressed with coordinates. The present embodiment is adapted to set an origin at a center position of the display screen 101, a Y coordinate in a vertical direction (+ direction is directed upward), an X coordinate in a horizontal direction (+ direction is to the right as one faces the screen), and a Z coordinate as depth (+ direction is directed frontward).

Figure 2:
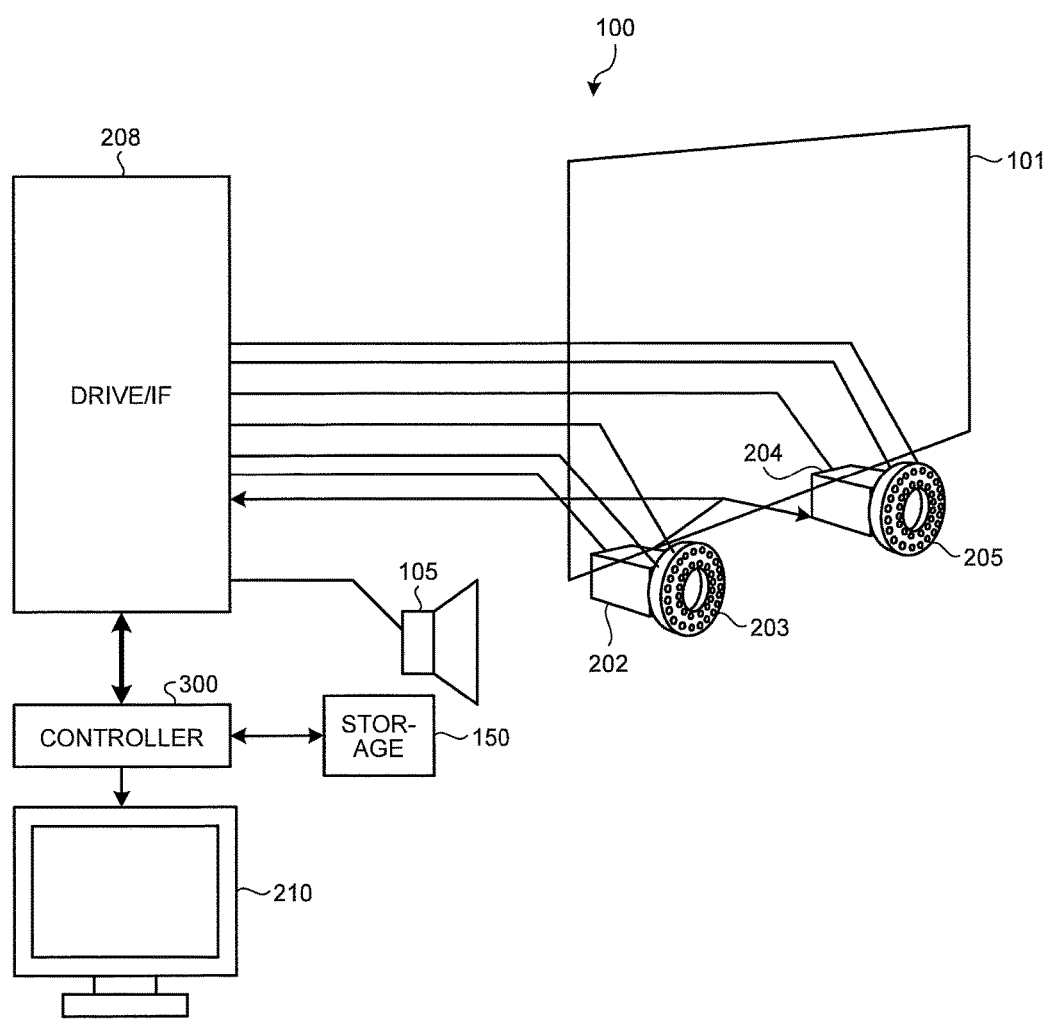
FIG. 2 is a diagram illustrating an overview of a function of a diagnosis supporting device according to the first embodiment.

FIG. 2 is a diagram illustrating an overview of a function of a diagnosis supporting device 100. FIG. 2 illustrates a part of the configuration illustrated in FIG. 1 as well as a configuration used to drive the configuration illustrated in FIG. 1. As illustrated in FIG. 2, the diagnosis supporting device 100 includes the right camera 202, the left camera 204, the infrared LED light sources 203 and 205, a speaker 105, a drive/IF (interface) 208, a controller 300, a storage 150, and a display 210. While the display screen 101 is illustrated in a way as illustrated in FIG. 2 to facilitate understanding of a positional relationship between the right camera 202 and the left camera 204, the display screen 101 is a screen displayed on the display 210. Note that the driver and the IF may be provided integrally or separately.

The speaker 105 functions as a sound output unit which outputs a sound to call attention of the subject at the time of calibration or the like.

The drive/IF 208 drives each unit included in the stereo camera 102. The drive/IF 208 further serves as an interface between each unit included in the stereo camera 102 and the controller 300.

The storage 150 stores various information such as a control program, a measurement result, and a diagnosis support result. The storage 150 for example stores an image displayed on the display 210. The display 210 displays various information such as a target image used in a diagnosis.

Figure 3:
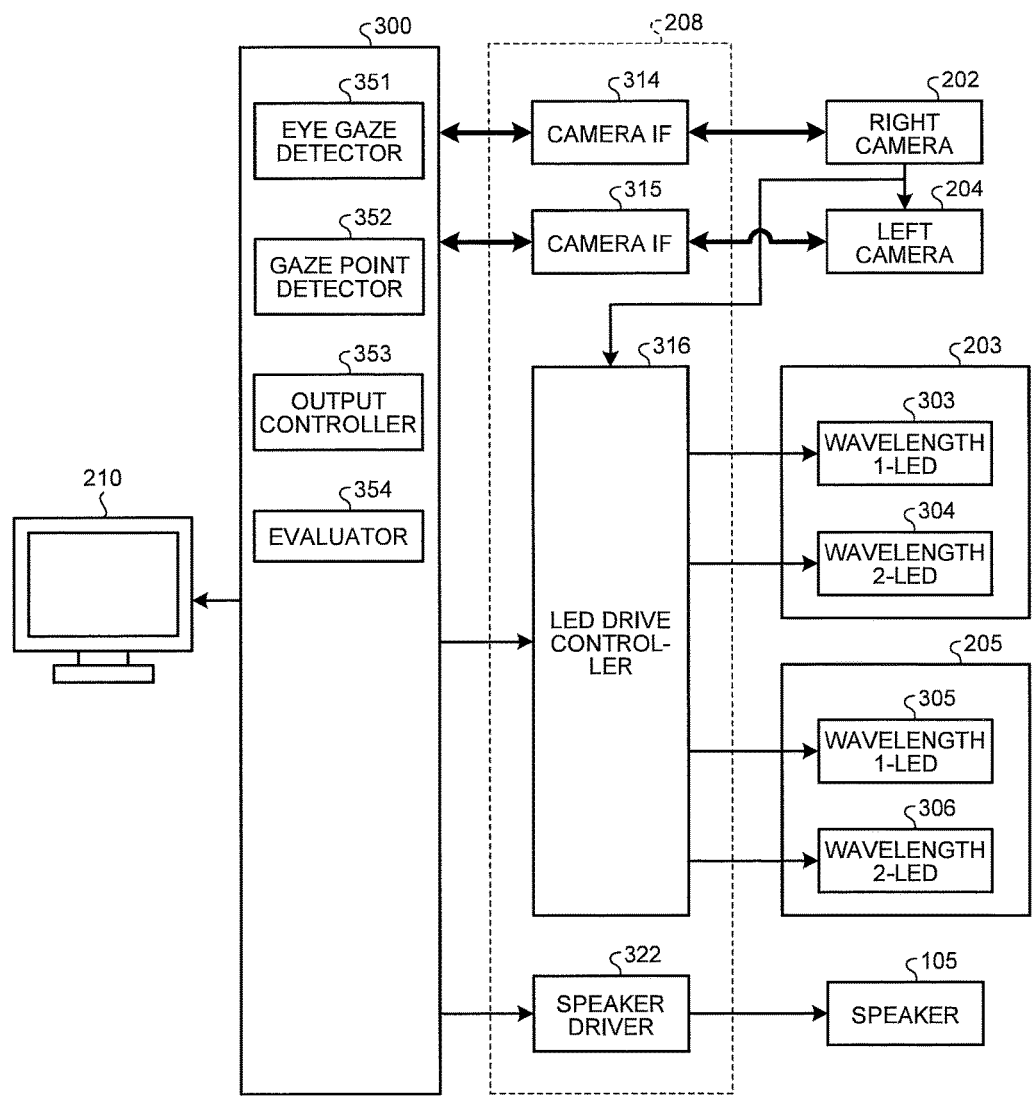
FIG. 3 is a block diagram illustrating an example of a detailed function of each unit illustrated in FIG. 2.

FIG. 3 is a block diagram illustrating an example of a detailed function of each unit illustrated in FIG. 2. The controller 300 is connected to the display 210 and the drive/IF 208 as illustrated in FIG. 3. The drive/IF 208 includes camera IFs 314 and 315, an LED drive controller 316, and a speaker driver 322.

The right camera 202 and the left camera 204 are connected to the drive/IF 208 through the camera IFs 314 and 315, respectively. The subject is imaged by these cameras that are driven by the drive/IF 208.

Figure 4:
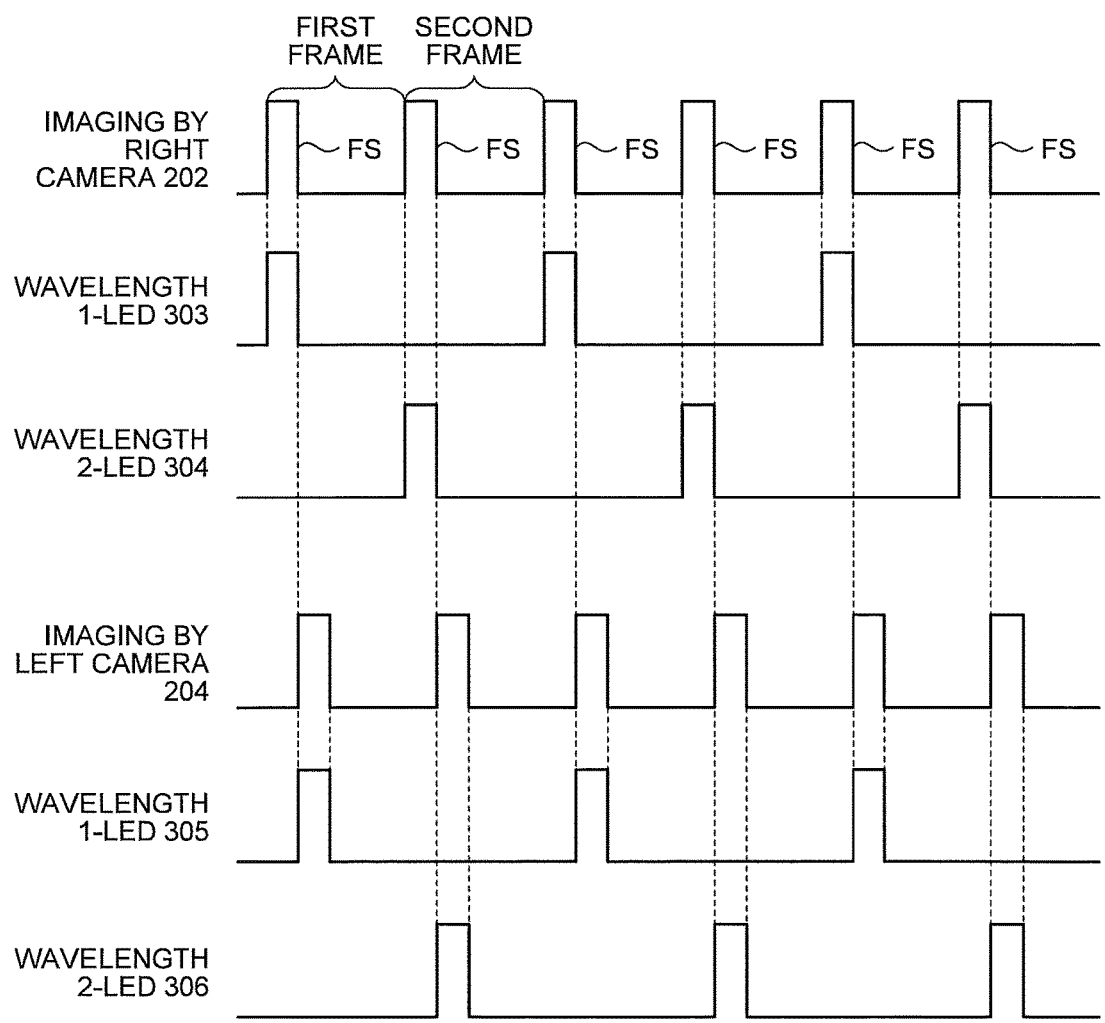
FIG. 4 is a diagram illustrating an example of relationship between an emission timing of an infrared light source and an imaging timing of left and right cameras.

FIG. 4 is a diagram illustrating an example of relationship between an emission timing of an infrared light source and an imaging timing of the left and right cameras. A frame synchronization signal FS is output from the right camera 202. The frame synchronization signal FS is input to the left camera 204 and the LED drive controller 316. As a result, infrared light sources with a wavelength 1 for the left and right cameras (wavelength 1-LED 303 and wavelength 1-LED 305) are emitted at different timings in a first frame to take in a corresponding image captured by the left and right cameras (the right camera 202 and the left camera 204), and in a second frame, infrared light sources with a wavelength 2 for the left and right cameras (wavelength 2-LED 304 and wavelength 2-LED 306) are emitted at different timings to take in a corresponding image captured by the left and right cameras. The processing in the first frame and second frame is repeated from then on according to the frame synchronization signal FS.

Referring back to FIG. 3, the infrared LED light source 203 includes the wavelength 1-LED 303 and the wavelength 2-LED 304. The infrared LED light source 205 includes the wavelength 1-LED 305 and the wavelength 2-LED 306.

The wavelength 1-LEDs 303 and 305 radiate an infrared ray with the wavelength 1. The wavelength 2-LEDs 304 and 306 radiate an infrared ray with the wavelength 2.

The wavelengths 1 and 2 for example correspond to wavelengths shorter than 900 nm and 900 nm or longer, respectively. When the infrared ray with the wavelength shorter than 900 nm is radiated to image a reflected light reflected off a pupil, there can be obtained a pupil image brighter than the one obtained when the infrared ray with the wavelength longer than or equal to 900 nm is radiated to image a reflected light reflected off the pupil. Note that the wavelength of the infrared ray being radiated is not limited to the aforementioned example as long as there is a difference between an outcome obtained by radiating the infrared ray with the wavelength 1 and imaging the reflected light reflected off the pupil and an outcome obtained by radiating the infrared ray with the wavelength 2 and imaging the reflected light reflected off the pupil.

The speaker driver 322 drives the speaker 105. The diagnosis supporting device 100 may also include an interface (printer IF) used to be connected to a printer as a printing unit. The diagnosis supporting device 100 may also be configured to incorporate a printer.

The controller 300 controls the entire diagnosis supporting device 100. The controller 300 includes an eye gaze detector 351, a gaze point detector 352, an output controller 353, and an evaluator 354.

The eye gaze detector 351 detects an eye gaze (eye gaze direction) of the subject from an image captured by an imaging unit (the stereo camera 102). Processing of eye gaze detection includes processing of detecting the position of an eye of the subject. The gaze point detector 352 detects a gaze point of the subject by using the eye gaze direction detected. The gaze point detector 352 detects the gaze point at which the subject gazes within a target image displayed on the display screen 101, for example. Various conventional methods can be applied as an eye gaze detection method used by the eye gaze detector 351 and a gaze point detection method used by the gaze point detector 352. There will be described an example where the stereo camera is used to detect the eye gaze direction and gaze point of the subject, as is the case with Patent Literature 3.

In this case, the eye gaze detector 351 detects the eye gaze direction of the subject from an image captured by the stereo camera 102. The eye gaze detector 351 detects the eye gaze direction of the subject by using the method disclosed in Patent Literature 1 and 2, for example. Specifically, the eye gaze detector 351 finds a difference between an image obtained by imaging during irradiation of the infrared ray with the wavelength 1 and an image obtained by imaging during irradiation of the infrared ray with the wavelength 2, and generates an image in which a pupil image is clearly shown. The eye gaze detector 351 uses two images generated in the aforementioned manner from images captured by the left and right cameras (right camera 202 and left camera 204), and calculates the position of the pupil of the subject (eye position) by using a method of stereoscopy. The eye gaze detector 351 further calculates the position of corneal reflection of the subject by using the image captured by each of the left and right cameras. After that, the eye gaze detector 351 calculates an eye gaze vector representing the eye gaze direction of the subject from the pupil position and corneal reflection position of the subject.

Note that the method of detecting the eye position and eye gaze of the subject is not limited to the aforementioned example. The eye position and eye gaze of the subject may be detected by analyzing an image captured by using visible light instead of the infrared ray, for example.

The gaze point detector 352 detects, as the gaze point of the subject, a point of intersection of the eye gaze vector expressed in a coordinate system illustrated in FIG. 1 and an XY plane, for example. When the eye gaze direction of each of both eyes is obtained, the gaze point may be measured by finding a point of intersection of left eye gaze and right eye gaze of the subject.

Figure 5:
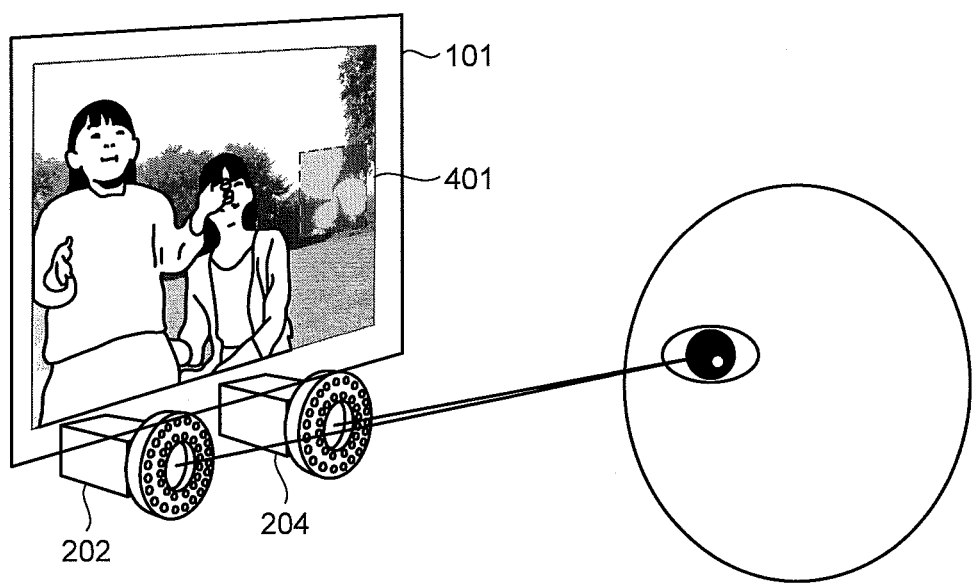
FIG. 5 is a diagram illustrating an example of detection of an eye and a distance when two cameras are used.

FIG. 5 is a diagram illustrating an example of detection of an eye and a distance when two cameras (right camera 202 and left camera 204) are used. The two cameras find in advance a camera parameter by applying a camera calibration theory based on a stereo calibration method. The stereo calibration method can apply various conventional methods such as a method using a Tsai's camera calibration theory. Three-dimensional coordinates of the eye in a world coordinate system are obtained by using the eye position detected from the image captured by the right camera 202, the eye position detected from the image captured by the left camera 204, and the camera parameter. As a result, one can estimate the distance between the eye and the stereo camera 102 as well as pupil coordinates. The pupil coordinates are coordinate values representing the position of the eye (pupil) of the subject on the XY plane. The pupil coordinates can be the coordinate values obtained by projecting the eye position represented in the world coordinate system onto the XY plane, for example. The pupil coordinates for both left and right eyes are usually obtained. A diagnostic image 401 is displayed on the display screen 101. As described later, the diagnostic image 401 includes a natural image displayed within a display area of the display screen 101 and a pattern image displayed in a partial area included in the display area and including a pattern similar to the natural image.

The pattern image is an image (geometric image) including one or more geometric patterns, for example. The natural image may be an image of a natural object or something associated with a natural object other than the geometric image. An image (still image or moving image) obtained by capturing a person, an animal, a plant and a natural scenery with a camera may be used as the natural image, for example. Moreover, an image (still image or moving image) of a character resembling a person or an animal may be used as the natural image.

Referring back to FIG. 3, the output controller 353 controls output of various information to the display 210 and the speaker 105. The output controller 353 for example controls output of the diagnostic image 401 and an evaluation result by the evaluator 354 to the display 210. The output controller 353 may display a plurality of diagnostic images as well. The output controller 353 may for example display, on the display 210, a first diagnostic image and then a second diagnostic image in which the position of a pattern image is different from that in the first diagnostic image. In this case, the gaze point detector 352 detects the gaze point of the subject when each of the first diagnostic image and the second diagnostic image is displayed. The plurality of diagnostic images is used to be able to more accurately perform detection of the gaze point and the diagnosis support.

The evaluator 354 calculates an evaluation value as an index pertaining to the degree of developmental disorder on the basis of the diagnostic image and the gaze point detected by the gaze point detector 352. The evaluator 354 for example calculates, as the evaluation value, a ratio of a time for which the subject looks at the natural image to a time for which the subject looks at the pattern image on the basis of the position of the gaze point of the subject when displaying diagnostic images illustrated in FIGS. 6 to 9 to be described, and calculates the evaluation value indicating a higher possibility of having the developmental disorder as the evaluation value is lower. The evaluator 354 may calculate the evaluation value on the basis of the diagnostic image and the gaze point and the calculation method is not limited to the present embodiment.

Figure 6:
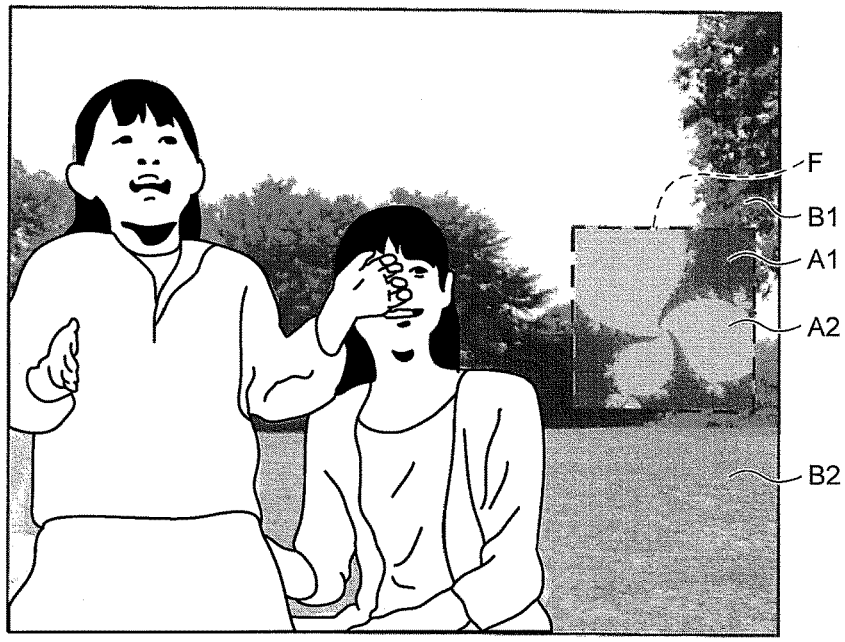
FIG. 6 is a diagram illustrating an example of a diagnostic image being displayed.
Figure 7:
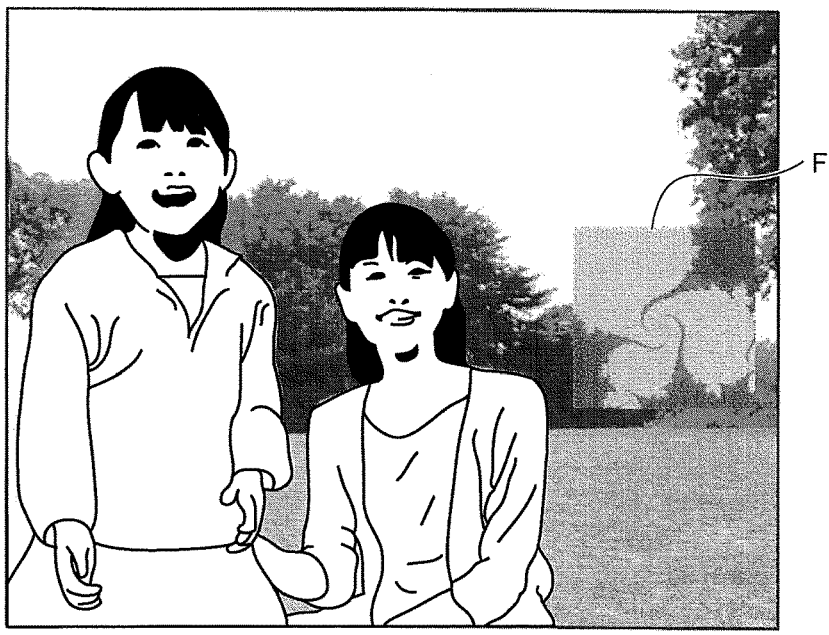
FIG. 7 is a diagram illustrating an example of the diagnostic image being displayed.
Figure 8:
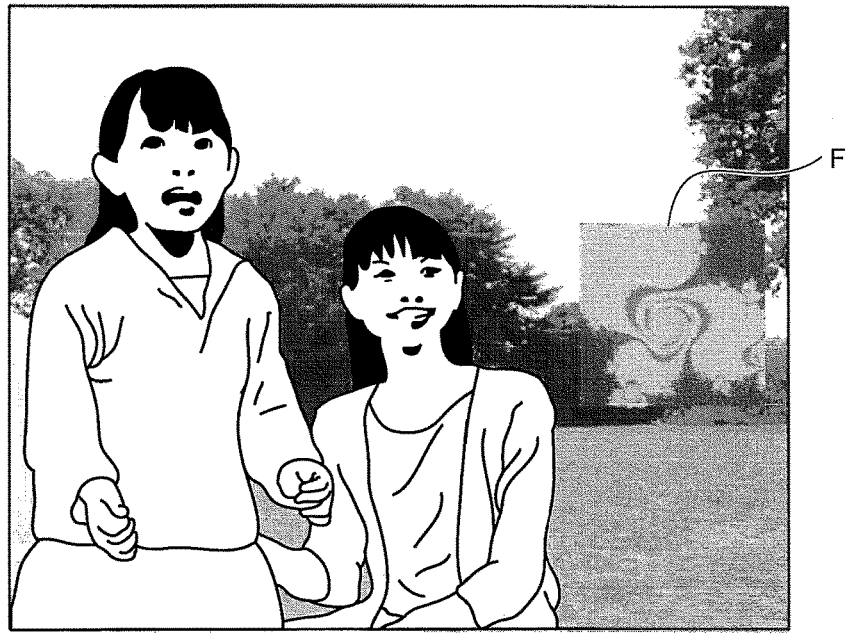
FIG. 8 is a diagram illustrating an example of the diagnostic image being displayed.
Figure 9:
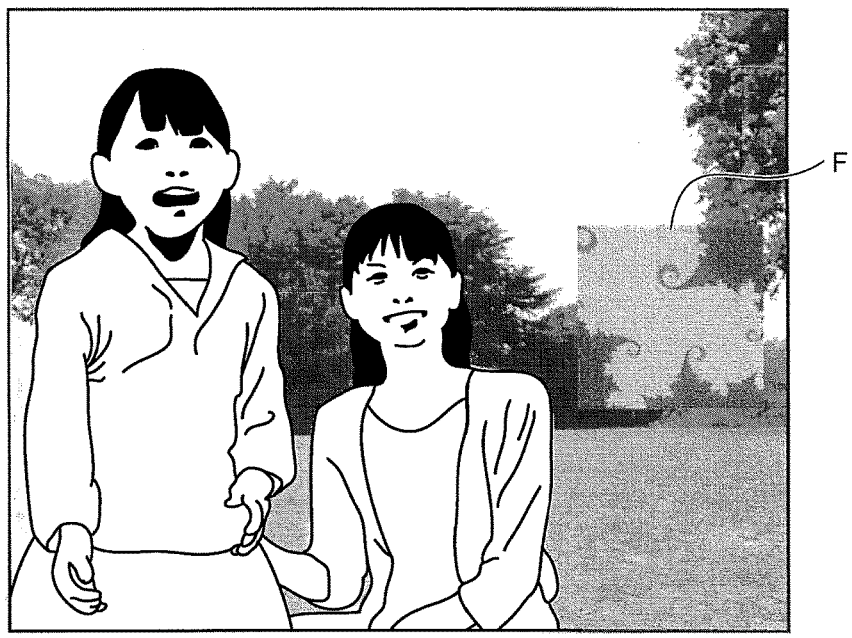
FIG. 9 is a diagram illustrating an example of the diagnostic image being displayed.

FIGS. 6 to 9 are diagrams each illustrating an example of the diagnostic image being displayed. There will be described an example where a moving image is used as the diagnostic image. Not only the moving image but also a plurality of still images may be used as the diagnostic image as well. FIG. 6 illustrates a video at the start of measurement. It is assumed that the individual calibration is completed before this moment. The calibration includes the aforementioned camera calibration as well as calibration performed for eye gaze detection (eye gaze detection calibration).

The present embodiment uses as the diagnostic image a video in which a video of a person (person video) occupies most of the display area. There is a strong tendency that such video is preferably viewed by a subject with typical development. A video of a geometric pattern (geometric pattern video) is displayed in a partial area F of this video. There is a strong tendency that the geometric pattern is preferably viewed by a subject with developmental disorder. It is confirmed as a result of an experiment that the subject with developmental disorder particularly prefers to view a fractal video containing a Julia set or a Mandelbrot set.

The video may be formed by composing two videos by picture-in-picture, or a video composed in advance may be reproduced as one video. The video may be formed such that the pattern image is superposed on the natural image. The video may also be composed such that a transparent pattern image is superposed on the natural image. The pattern image can be less conspicuous by making the natural image transparent.

What is important here is that the video of the area F does not apparently stand out too much from the surrounding video of the person. This allows the subject with typical development to pay more attention to the person and thus leads to a decreased probability that the subject gazes at the area F. The subject with developmental disorder can find the area F quickly even in this situation. The difference in positions of the gaze points between the two subjects is made clearer as a result.

In the conventional method where the person video and the geometric pattern video are arranged on left and right sides of the screen, the subject often tends to preferably look at either one of the two videos while comparing the two, but it has been difficult in some cases to detect a difference in the preference.

Accordingly, in the present embodiment, at least one of brightness, hue and chroma of the area F is similar to or matches that of a part of the area outside the area F in order to make the area F less conspicuous. That is, the output controller 353 performs control such that a partial image displayed in an area adjacent to the partial area within the partial image included in the natural image is displayed in a display mode similar to or matching a display mode of the pattern image. The display mode is not limited to the brightness, hue and chroma. Display modes such as color tone, shape and motion speed may be made similar to or match that of the pattern image as well.

In terms of the hue in a Munsell color system where a Munsell hue circle with 20 colors is adapted, three colors adjacent to a certain color on both sides correspond to a preferable range of similarity. The range of similarity for red includes purple with a tinge of red, reddish purple, red with a tinge of purple, red with a tinge of yellow, yellowish red, and yellow with a tinge of red, for example. The preferable range of similarity corresponds to within three values for the brightness (value) and six chromas for the chroma in the Munsell color system.

A geometric pattern A1 within the area F in FIG. 6 has the brightness, hue and chroma close to those of the area F and a part B1 (tree) in the vicinity of the area F in the natural image. A geometric pattern A2 within the area F has the brightness, hue and chroma close to those of the area F and a part B2 (turf) in the vicinity of the area F in the natural image. The areas of interest such as A2 and B2 may be slightly separated from each other instead of being adjacent to each other. This allows the video of the area F to blend into the natural image and be less conspicuous.

Moreover, the part of pattern A1 and the part B1 in FIG. 6 are displayed almost continuously as a pattern. More specifically, the outlines of the part B1 and the part of pattern A1 are displayed almost continuously where the part B1 is a part of a tree that is an object included in the natural image. The part of pattern A1 is displayed as though forming the tree (object) in the series of natural images. This allows the area F to be less conspicuous. The geometric pattern displayed continuously with the surrounding as illustrated in FIG. 6 is a more preferable combination of videos. Note that the object is an image of the tree or person in FIG. 6, for example.

FIGS. 6 to 9 illustrate a change in sequential screens. FIGS. 6 to 9 are examples of four images extracted from a video that changes within a few seconds, for example. A fractal video changing gradually is displayed in a predetermined area (area F) within a video including the person video. The motion speed of the gradually changing fractal video may be similar to or match the motion speed of the object in the natural image. The subject is less likely to notice a motion of the pattern image by having the similar or matching motion speeds. Note that the object is the image of the tree or person in FIG. 6, for example.

Figure 10:
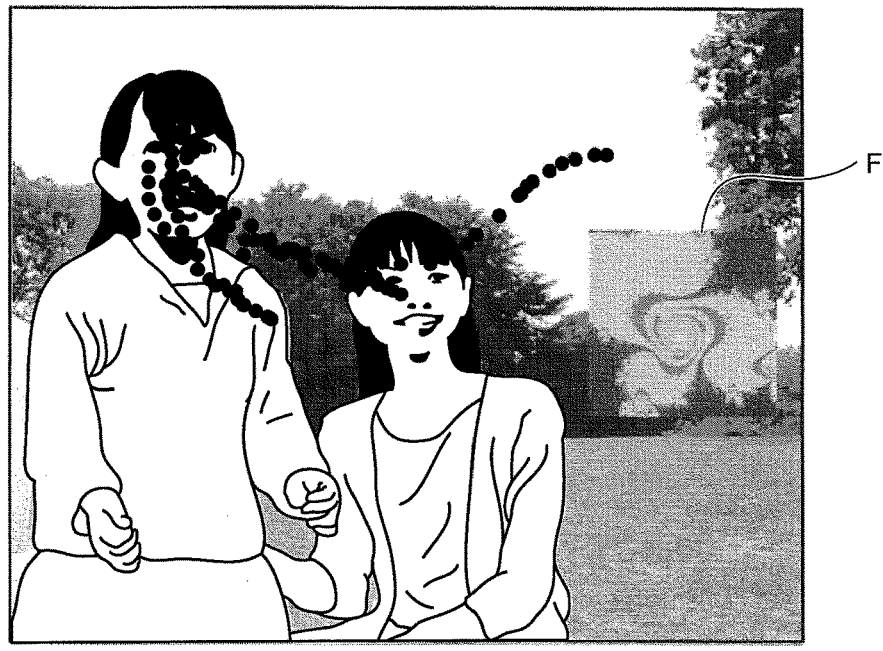
FIG. 10 is a diagram illustrating a movement of a gaze point of a subject with typical development viewing an image.

FIG. 10 is a diagram illustrating an example of a movement (distribution) of a gaze point of the subject with typical development viewing the image with the diagnosis supporting device 100. A trail of black dots illustrates the movement of the gaze point. There is a high probability that the subject with typical development gazes at the persons. Moreover, the subject with typical development does not notice the geometric pattern blending into the background much.

Figure 11:
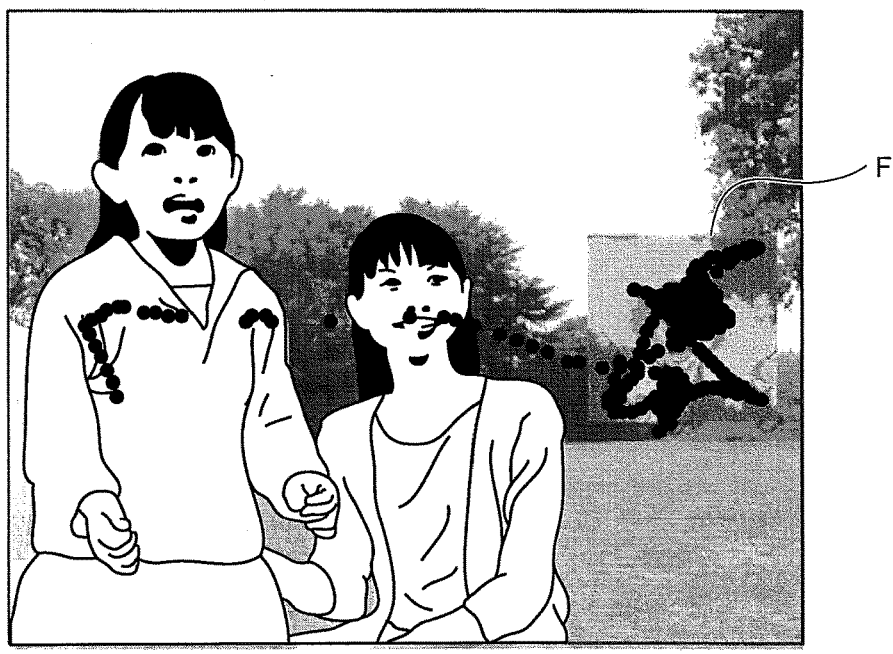
FIG. 11 is a diagram illustrating a movement of a gaze point of a subject with developmental disorder viewing an image.

FIG. 11 is a diagram illustrating an example of the movement (distribution) of the gaze point of the subject with developmental disorder viewing the image with the diagnosis supporting device 100. A trail of black dots illustrates the movement of the gaze point. There is a low probability that the subject with developmental disorder gazes at the persons. On the other hand, there is a high probability that the subject with developmental disorder notices the geometric pattern blending into the background and gazes at an area (area F) including the pattern.

Figure 12:
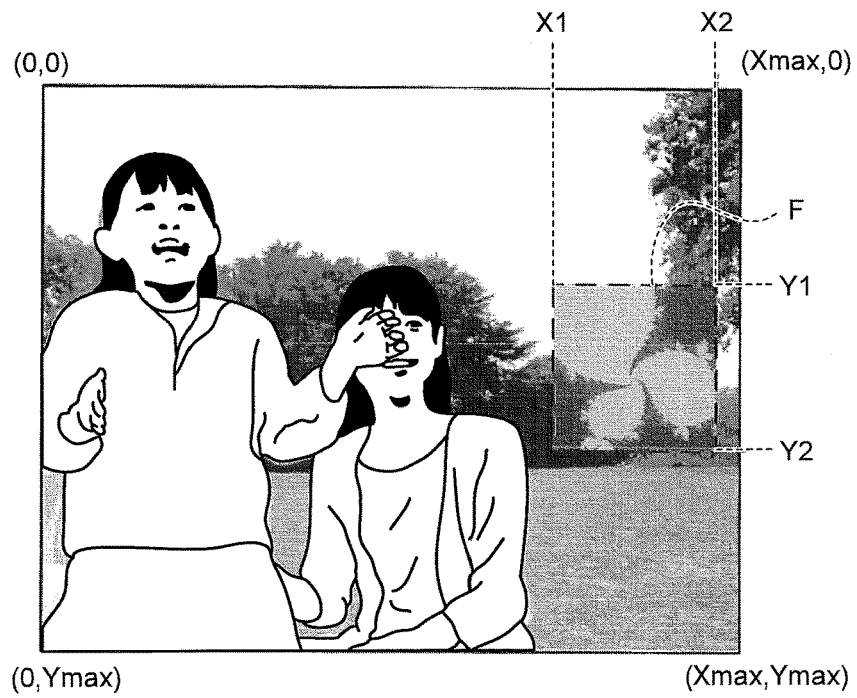
FIG. 12 is a diagram illustrating coordinates of an image displayed in the display.

FIG. 12 is a diagram illustrating coordinates and the like of the image displayed in the display 210. For the sake of description, the coordinates on the display 210 have an origin at an upper left corner, a Y coordinate in a vertical direction (+ direction is directed downward) and an X coordinate in a horizontal direction (+ direction is to the right as one faces the image). This is different from the aforementioned world coordinate (spatial coordinate) used to detect the gaze point.

The pixel count of the display 210 equals Xmax×Ymax in the example illustrated in FIG. 12. It is assumed for the area F that the X coordinate of a left side is X1, the X coordinate of a right side is X2, the Y coordinate of an upper side is Y1, and the Y coordinate of a lower side is Y2. Details of diagnostic processing using these video and coordinates will be described with reference to flowcharts illustrated in FIGS. 14 to 16 (to be described).

Figure 13:
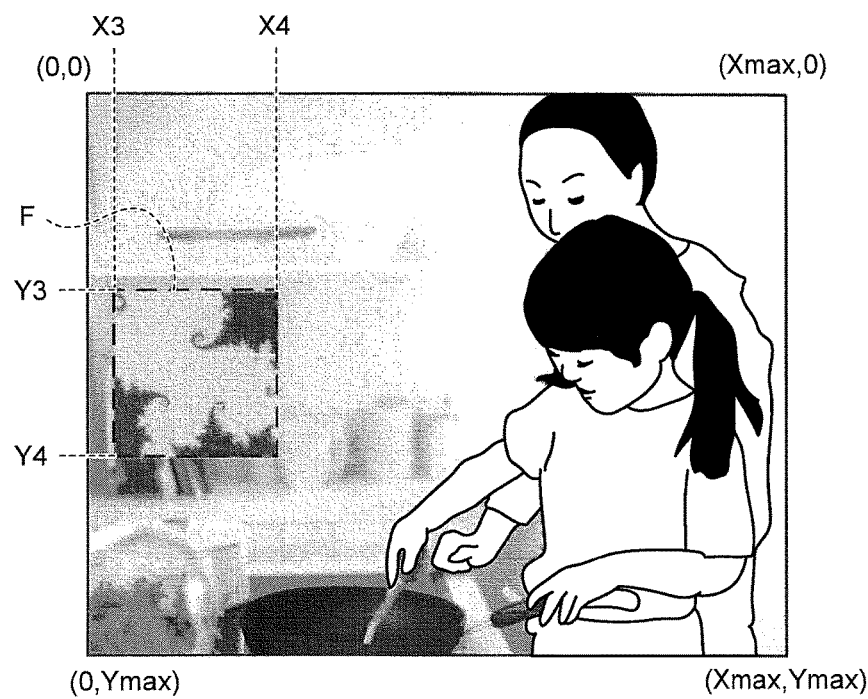
FIG. 13 is a diagram illustrating an example of a diagnostic image different from FIGS. 6 to 12.

FIG. 13 is a diagram illustrating an example of a video (diagnostic image) different from the video (FIGS. 6 to 12) used in the description up to this point. The output controller 353 performs control to display the video illustrated in FIGS. 6 to 12 as the first diagnostic image and then display the video illustrated in FIG. 13 as the second diagnostic image, for example.

It is assumed for an area F that the X coordinate of a left side is X3, the X coordinate of a right side is X4, the Y coordinate of an upper side is Y3, and the Y coordinate of a lower side is Y4. Details of diagnostic processing using these video and coordinates will be described with reference to the flowcharts illustrated in FIGS. 14 to 16 (to be described).

Note that the position of the area F in the diagnostic image is different in FIGS. 12 and 13. Specifically, the areas F are symmetrical about the point of symmetry being the center of the display area of the display screen 101. The areas F may be symmetrical to the center of the display area of the display screen 101. Such display allows one to diagnose a viewing tendency of the subject such as from which direction the subject looks at the screen.

Figure 14:
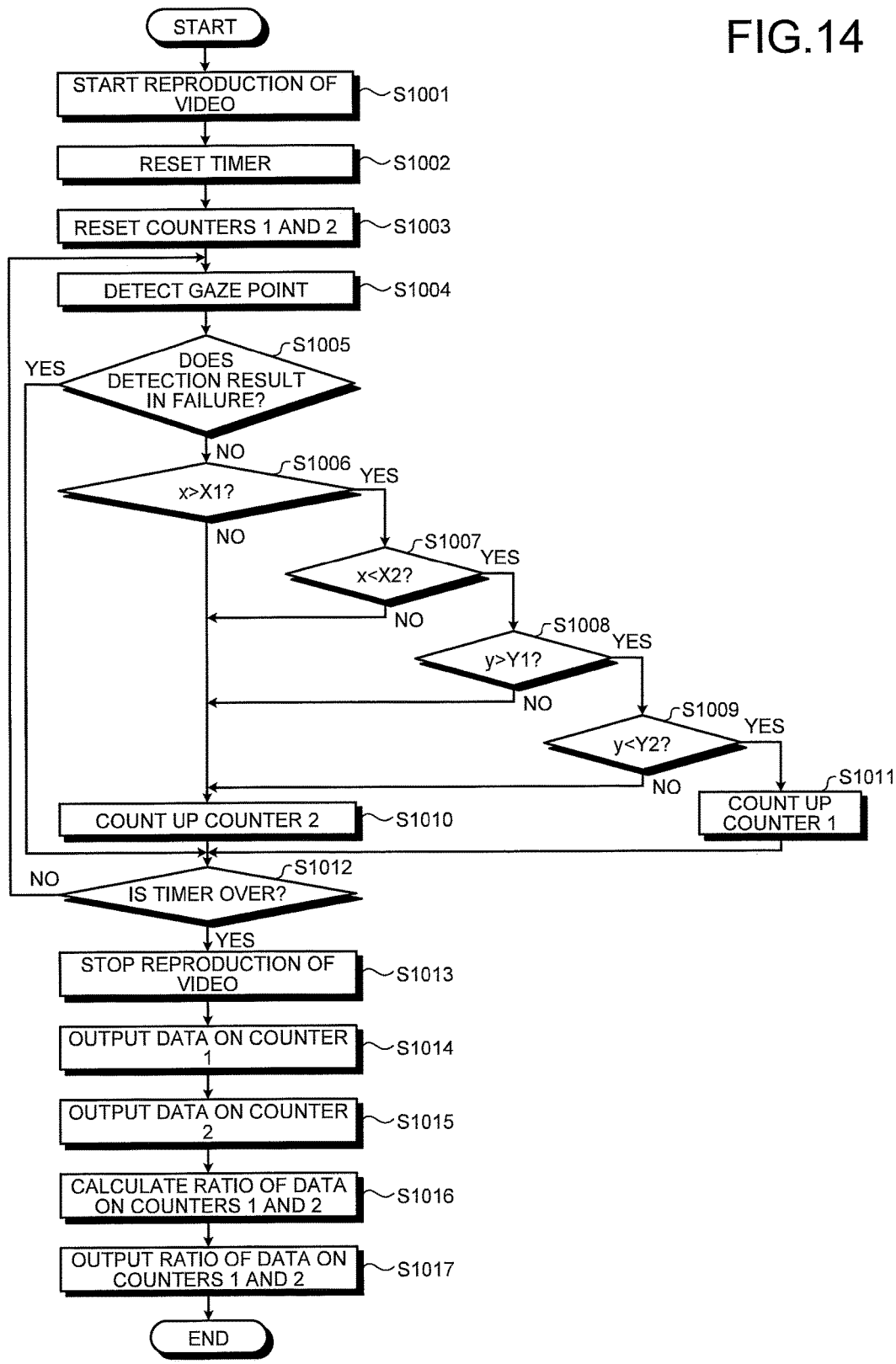
FIG. 14 is a flowchart illustrating an example of diagnosis support processing according to the first embodiment.
Figure 15:
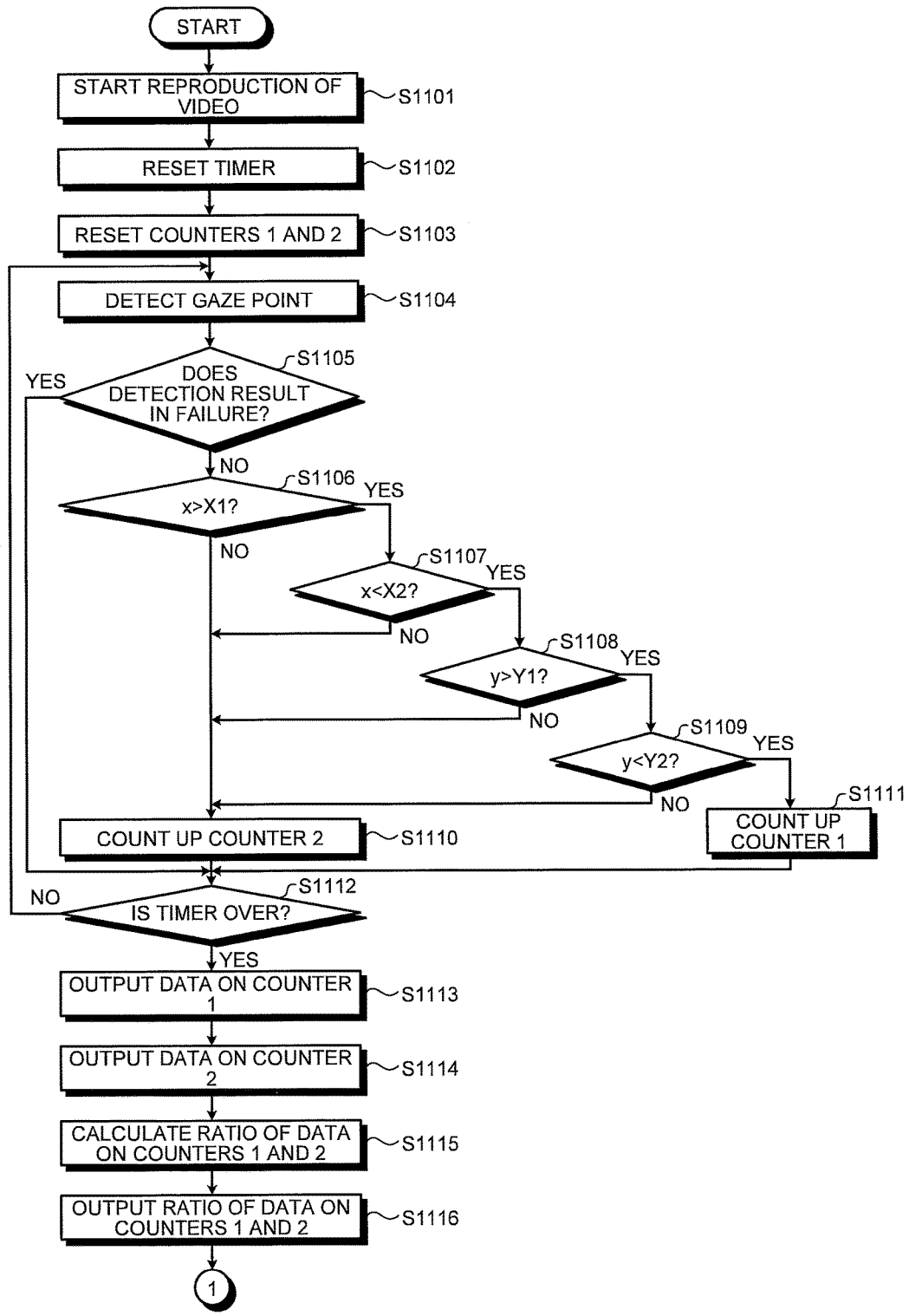
FIG. 15 is a flowchart illustrating an example of the diagnosis support processing according to the first embodiment.
Figure 16:
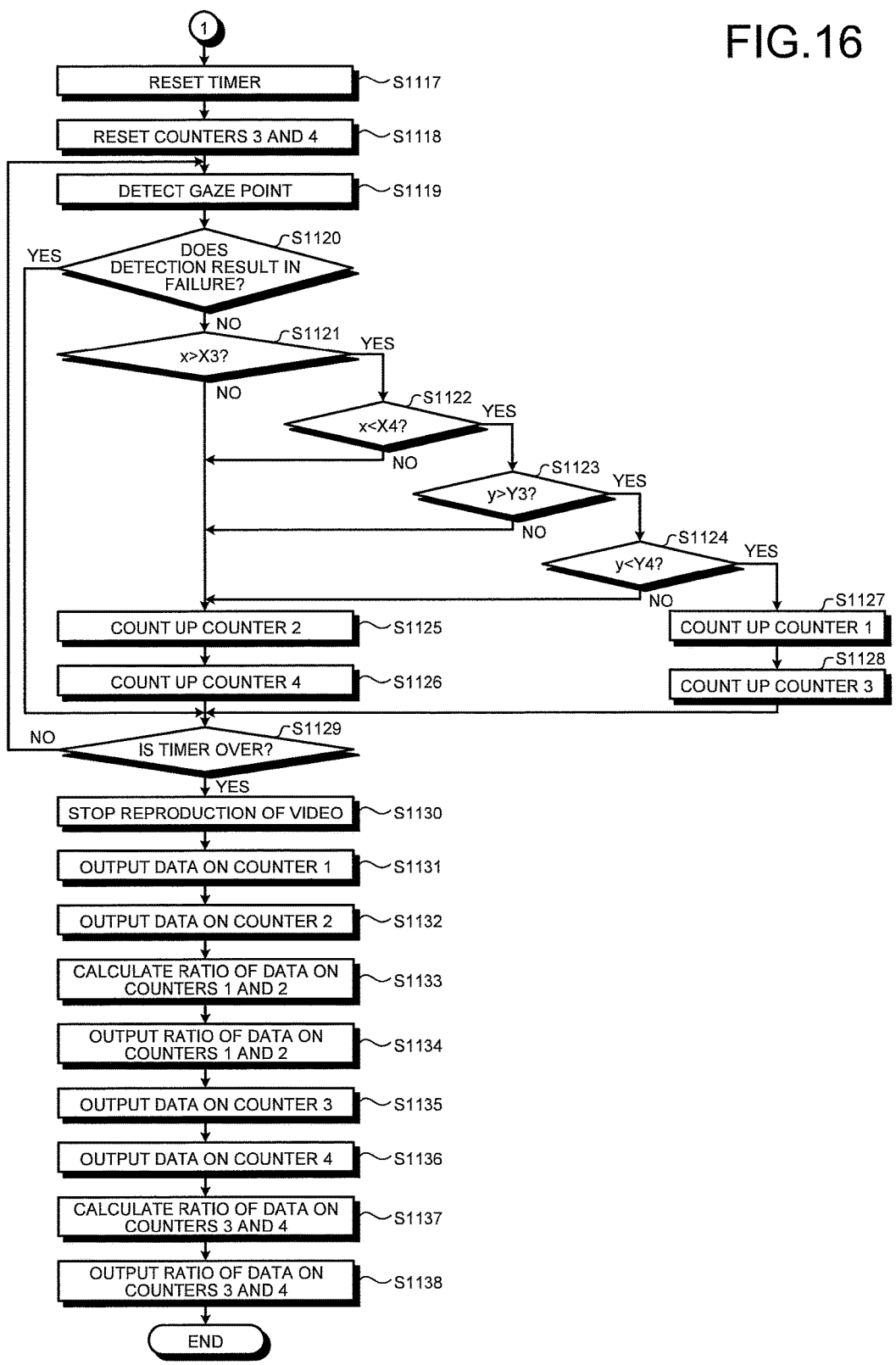
FIG. 16 is a flowchart illustrating an example of the diagnosis support processing according to the first embodiment.

Next, diagnosis support processing performed with the diagnosis supporting device 100 according to the first embodiment configured in the aforementioned manner will be described with reference to FIGS. 14 to 16. FIGS. 14 to 16 are the flowcharts each illustrating the example of the diagnosis support processing according to the present embodiment.

FIG. 14 will be referenced first to describe a flowchart when a single video is used to perform the diagnosis support. It is hereinafter assumed that the natural image (including the person video) and the geometric pattern video are composed together in advance.

First, the controller 300 starts reproduction of the video (step S1001). The controller 300 then resets a timer which measures a time slightly shorter than the reproduction time of the video (step S1002). Next, the controller 300 resets a counter 1 which counts up when a part within the area F is gazed at and a counter 2 which counts up when a part outside the area F is gazed at (step S1003).

Note that the gaze point measurement described below is performed for each frame of the stereo camera 102 which synchronously performs imaging, for example. That is, the gaze point is measured at every predetermined time interval. Count values of the counters 1 and 2 therefore correspond to times for which the part within the area F and the part outside the area F are gazed at, respectively, Next, the eye gaze detector 351 and the gaze point detector 352 perform gaze point detection (step S1004). The controller 300 thereafter determines whether or not the gaze point detection results in failure (step S1005). The gaze point detection results in failure when the image of the pupil and corneal reflection cannot be obtained due to a blink, for example. The gaze point detection also results in failure when the gaze point is not present in the screen of the display 210 (the subject looks outside the screen of the display 210).

When the gaze point detection fails (step S1005: Yes), processing in each of steps S1006 to S1011 is skipped to proceed to step S1012 in order not to affect the counters 1 and 2.

When the gaze point detection succeeds (step S1005: No), the controller 300 examines whether an X coordinate "x" of the gaze point on the display 210 is larger than X1 (step S1006). When "x" is larger than X1 (step S1006: Yes), the controller 300 examines whether "x" is smaller than X2 (step S1007). When "x" is smaller than X2 (step S1007: Yes), the controller 300 examines whether a Y coordinate "y" of the gaze point on the display 210 is larger than Y1 (step S1008). When "y" is larger than Y1 (step S1008: Yes), the controller 300 examines whether "y" is smaller than Y2 (step S1009). The gaze point is present within the area F when "y" is smaller than Y2 (step S1009: Yes). The controller 300 therefore counts up the counter 1 (step S1011). The subject looks at the person video or the like outside the area F when "y" is not smaller than Y2 (step S1009: No). The controller 300 therefore counts up the counter 2 (step S1010). Likewise, the controller 300 counts up the counter 2 (step S1010) when "x" is not larger than X1 (step S1006: No), "x" is not smaller than X2 (step S1007: No), and "y" is not larger than Y1 (step S1008: No).

Next, the controller 300 examines whether the timer is over in order to confirm the end of the video (step S1012). The controller 300 determines that the timer is over when the value thereof reaches a predetermined value corresponding to an end time of the video, for example. The processing returns to step S1004 to repeat the aforementioned processing when the timer is not over (step S1012: No).

When the timer is over (step S1012: Yes), the controller 300 stops the reproduction of the video (step S1013). The controller 300 then outputs data (value) on the counter 1 (step S1014). The data on the counter 1 corresponds to the time for which the part within the area F is gazed at. The controller 300 then outputs data on the counter 2 (step S1015). The data on the counter 2 corresponds to the time for which the part outside the area F is gazed at. Next, the evaluator 354 calculates a ratio of the counter 1 to the counter 2 (step S1016). The evaluator 354 for example calculates an evaluation value representing a ratio of the value on the counter 1 with respect to the value on the counter 2. This evaluation value serves as an index of possibility of having the developmental disorder. The method of calculating the evaluation value is not limited to the aforementioned example. Any evaluation value may be used as long as the value can determine which of the natural image and the pattern image the subject gazes at. The higher the ratio of gazing at the area F, the higher the possibility of having the developmental disorder. The evaluator 354 outputs the evaluation value being calculated (step S1017).

FIGS. 15 and 16 are flowcharts when two videos are used to perform the diagnosis support. As with FIG. 14, it is assumed that the natural image (including the person video) and the geometric pattern video are composed together in advance. Moreover, the two videos are connected where each video is constructed to have a predetermined duration.

FIG. 15 corresponds to processing performed when a first video (video 1) of the two videos is displayed. Steps S1101 to S1112 are similar to steps S1001 to S1012 illustrated in FIG. 14. Processing corresponding to step S1013 in FIG. 14 is deleted in FIG. 15 since the reproduction of the video is not yet stopped. Steps S1113 to S1116 are similar to steps S1014 to S1017 illustrated in FIG. 14. The role of each of the counters 1 and 2 is different from that of FIG. 14 in this example.

The counters 1 and 2 in FIGS. 15 and 16 count during time for which the two videos being the video 1 (first diagnostic image) and a video 2 (second diagnostic image) are reproduced. That is, the counters perform count for the two videos as a whole. Here, a count result and a ratio thereof for the video 1 are output at the end of the video 1 (steps S1113 to S1116). The counting is then continued for the video 2, and a total value is output (step S1131 to S1134).

FIG. 16 will now be described. FIG. 16 corresponds to processing performed when the second video (video 2) of the two videos is displayed. Reproduction of the video 2 is started immediately before step S1117.

The controller 300 resets a timer which measures a time slightly shorter than the reproduction time of the video 2 (step S1117). Next, the controller 300 resets a counter 3 which counts up when a part within the area F in the video 2 is gazed at and a counter 4 which counts up when a part outside the area F is gazed at (step S1118).

Next, the eye gaze detector 351 and the gaze point detector 352 perform gaze point detection (step S1119). The controller 300 thereafter determines whether or not the gaze point detection results in failure (step S1120).

When the gaze point detection fails (step S1120: Yes), processing in each of steps S1121 to S1128 is skipped to proceed to step S1129 in order not to affect the counters 3 and 4.

When the gaze point detection succeeds (step S1120: No), the controller 300 examines whether an X coordinate "x" of the gaze point on the display 210 is larger than X3 (step S1121). When "x" is larger than X3 (step S1121: Yes), the controller 300 examines whether "x" is smaller than X4 (step S1122). When "x" is smaller than X4 (step S1122: Yes), the controller 300 examines whether a Y coordinate "y" of the gaze point on the display 210 is larger than Y3

(step S1123). When "y" is larger than Y3 (step S1123: Yes), the controller 300 examines whether "y" is smaller than Y4 (step S1124). The gaze point is present within the area F when "y" is smaller than Y4 (step S1124: Yes). The controller 300 therefore counts up the counter 1 (step S1127) and counts up the counter 3 (step S1128). The subject looks at the person video or the like outside the area F when "y" is not smaller than Y4 (step S1124: No). The controller 300 therefore counts up the counter 2 (step S1125) and counts up the counter 4 (step S1126).

Next, the controller 300 examines whether the timer is over in order to confirm the end of the video (step S1129). The processing returns to step S1119 to repeat the aforementioned processing when the timer is not over (step S1129: No).

When the timer is over (step S1129: Yes), the controller 300 stops the reproduction of the video (step S1130). The controller 300 then outputs data on the counter 1 (step S1131). The data on the counter 1 corresponds to the time for which the part within the area F is gazed at when the videos 1 and 2 are reproduced. The controller 300 then outputs data on the counter 2 (step S1132). The data on the counter 2 corresponds to the time for which the part outside the area F is gazed at when the videos 1 and 2 are reproduced. Next, the evaluator 354 calculates an evaluation value representing a ratio of the counter 1 to the counter 2 (step S1133). The evaluator 354 outputs the evaluation value (step S1134).

The controller 350 also outputs data on the counter 3 (step S1135). The data on the counter 3 corresponds to the time for which the part within the area F is gazed at in the video 2. Next, the controller 350 outputs data on the counter 4 (step S1136). The data on the counter 4 corresponds to the time for which the part outside the area F is gazed at in the video 2. Next, the evaluator 354 calculates an evaluation value representing a ratio of the counter 3 to the counter 4 (step S1137). The evaluator 354 outputs the evaluation value (step S1138).

One can know the tendency of the subject by comparing a count result and the ratio thereof for the video 1 (steps S1113 to S1116) and a count result and the ratio thereof for the video 2 (steps S1135 to S1138). When the subject tends to look from the right side of the screen, for example, the count value within the area F tends to increase in the video 1 and decrease in the video 2. When both sides are looked at in balance, the subject is thought to start looking from the center part and then gaze at a part according to his preferences.

It has been described in the first embodiment that the evaluation using the videos 1 and 2 is used to know the tendency of the subject gazing at the screen. A larger or smaller value may be adopted, while using the videos 1 and 2, to serve as the final evaluation value indicating the ratio of gazing at the area F. Moreover, the final evaluation value may be found by averaging two evaluation values.

The following effects can be attained according to the first embodiment, for example.

(1) The area of the geometric pattern is arranged in the person video, formed while combined with the part of the video outside the area, and made to gradually change in shape, the area having the display mode such as the brightness, hue and chroma close to that of the video part outside the area. As a result, the typical subject is less likely to notice the area whereas the subject with developmental disorder can accurately find the area. This increases the difference in the gaze points and thus improves the detection accuracy as compared to the conventional art.

(2) The measurement is performed the plurality of times while changing the geometric pattern area symmetrically about the center of the screen. This can cancel the tendency of the subject who tends to look at a specific direction.

Moreover, in the modes illustrated in FIGS. 6 to 9 of the present invention, the video can be largely displayed in full screen compared to a method in which the person video and the geometric pattern video are displayed in two screens on left and right sides, whereby the measurement accuracy is improved as a subject with poor eyesight can easily view the video.

Second Embodiment

A second embodiment realizes an eye gaze detection apparatus and an eye gaze detection method which can further simplify the apparatus configuration compared to the first embodiment.

The eye gaze detection apparatus and the eye gaze detection method of the second embodiment will now be described in detail with reference to the drawings. The present invention is not to be limited by the embodiment. Moreover, there will be described an example where the eye gaze detection apparatus is used as a diagnosis supporting device which supports a diagnosis of developmental disorder or the like by using an eye gaze detection result. The eye gaze detection apparatus is not limited only to the diagnosis supporting device.

The eye gaze detection apparatus (diagnosis supporting device) of the present embodiment detects an eye gaze by using an illuminator installed at one place. Moreover, the eye gaze detection apparatus (diagnosis supporting device) of the present embodiment calculates a corneal curvature center position highly accurately by using a measurement result obtained by causing a subject to gaze at one point before the eye gaze detection.

The illuminator includes a light source and is an element capable of irradiating light onto an eyeball of the subject. The light source is an element such as an LED (Light Emitting Diode) generating light. The light source may be formed of one LED or formed by arranging a plurality of LEDs combined at one place. The "light source" will be hereinafter used in some cases as a term representing the illuminator.

Figure 17:
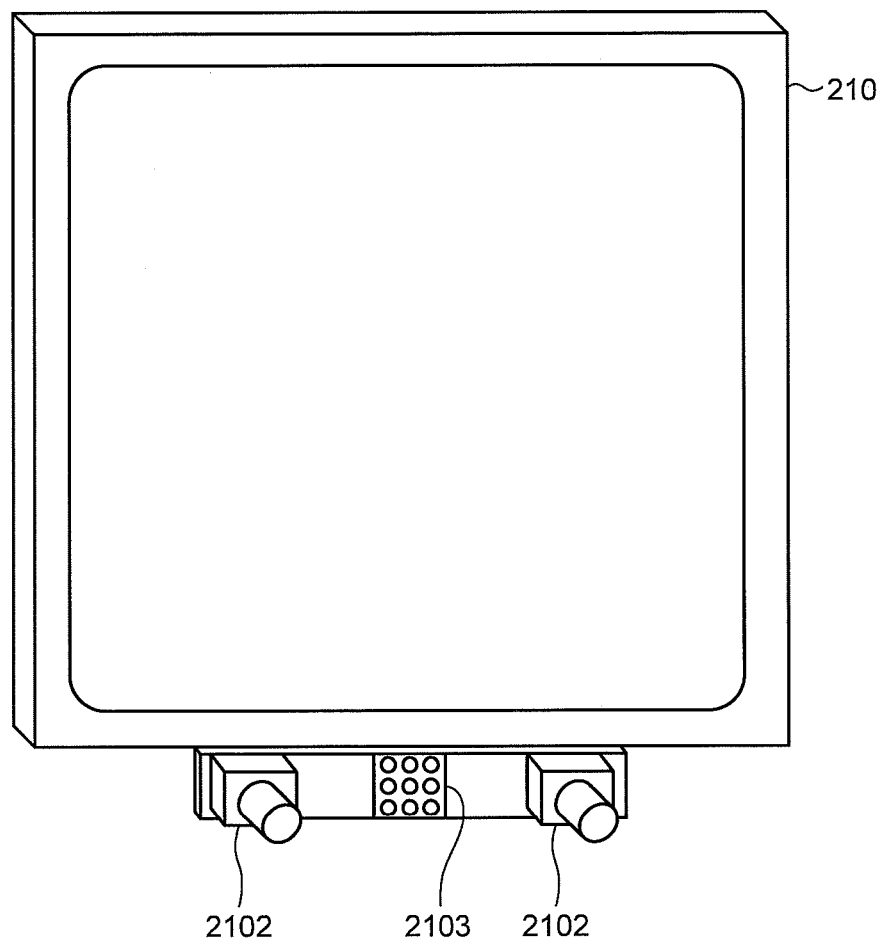
FIG. 17 is a diagram illustrating an example of arrangement of a display, a stereo camera, and an infrared light source according to a second embodiment.
Figure 18:
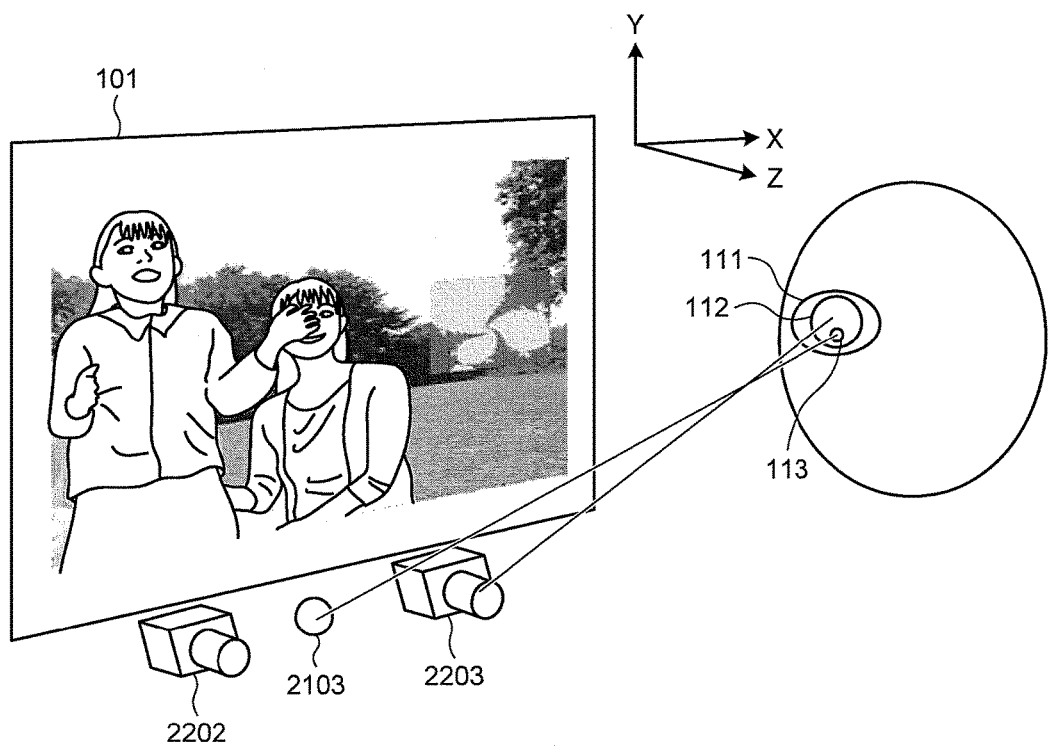
FIG. 18 is a diagram illustrating an example of arrangement of the display, the stereo camera, the infrared light source and the subject according to the second embodiment.

FIGS. 17 and 18 are diagrams each illustrating an example of arrangement of a display, a stereo camera, an infrared light source and the subject according to the second embodiment. The same reference numeral will be denoted to a same configuration as that of the first embodiment to omit description of such configuration in some cases.

The diagnosis supporting device of the second embodiment includes a display 210, a stereo camera 2102, and an LED light source 2103 as illustrated in FIG. 17. The stereo camera 2102 is arranged below the display 210. The LED light source 2103 is arranged at the center of two cameras included in the stereo camera 2102. The LED light source 2103 is a light source irradiating a near infrared ray with the wavelength of 850 nm, for example. FIG. 17 illustrates an example where the LED light source 2103 (illuminator) is formed of nine LEDs. The stereo camera 2102 uses a lens capable of transmitting near infrared light with the wavelength of 850 nm.

The stereo camera 2102 includes a right camera 2202 and a left camera 2203 as illustrated in FIG. 18. The LED light source 2103 irradiates the near infrared light toward an eyeball 111 of the subject. An image obtained by the stereo camera 2102 shows a dark pupil 112 reflected with low brightness and bright corneal reflection 113 reflected with high brightness and generated as a virtual image within the eyeball 111. As a result, the position of each of the pupil 112 and the corneal reflection 113 on the image can be obtained by the two cameras (the right camera 2202 and the left camera 2203).

A three-dimensional world coordinate value of the position of each of the pupil 112 and the corneal reflection 113 is further calculated from the positions of the pupil 112 and the corneal reflection 113 obtained by the two cameras. The present embodiment is adapted to set, as the three-dimensional world coordinates, an origin at a center position of a display screen 101, a Y coordinate in a vertical direction (+ direction is directed upward), an X coordinate in a horizontal direction (+ direction is to the right as one faces the screen), and a Z coordinate as depth (+ direction is directed frontward).

Figure 19:
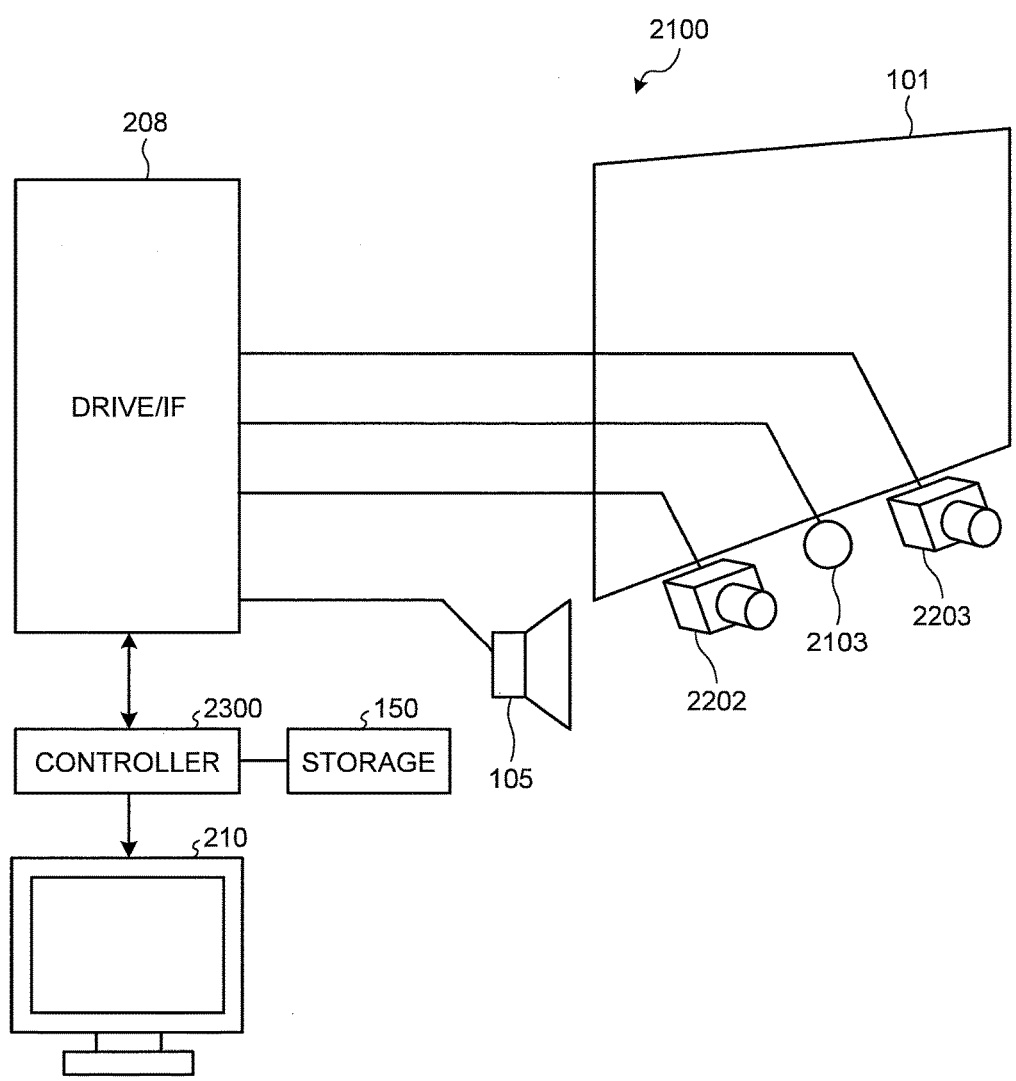
FIG. 19 is a diagram illustrating an overview of a function of a diagnosis supporting device.

FIG. 19 is a diagram illustrating an overview of a function of a diagnosis supporting device 2100 according to the second embodiment. FIG. 19 illustrates a part of the configuration illustrated in FIGS. 17 and 18 as well as a configuration used to drive the configuration illustrated in FIGS. 17 and 18. As illustrated in FIG. 19, the diagnosis supporting device 2100 includes the right camera 2202, the left camera 2203, the LED light sources 2103, a speaker 105, a drive/IF (interface) 208, a controller 2300, a storage 150, and the display 210. While the display screen 101 is illustrated in a way as illustrated in FIG. 19 to facilitate understanding of a positional relationship between the right camera 2202 and the left camera 2203, the display screen 101 is a screen displayed on the display 210. Note that the driver and the IF may be provided integrally or separately.

The speaker 105 functions as a sound output unit which outputs a sound to call attention of the subject at the time of calibration or the like.

The drive/IF 208 drives each unit included in the stereo camera 2102. The drive/IF 208 further serves as an interface between each unit included in the stereo camera 2102 and the controller 2300.

The controller 2300 can be realized by, for example, a computer including a controller such as a CPU (Central Processing Unit), a storage such as a ROM (Read Only Memory) and a RAM (Random Access Memory), a communication I/F performing communication by connecting to a network, and a bus connecting each unit.

The storage 150 stores various information such as a control program, a measurement result, and a diagnosis support result. The storage 150 for example stores an image displayed on the display 210. The display 210 displays various information such as a target image used in a diagnosis.

Figure 20:
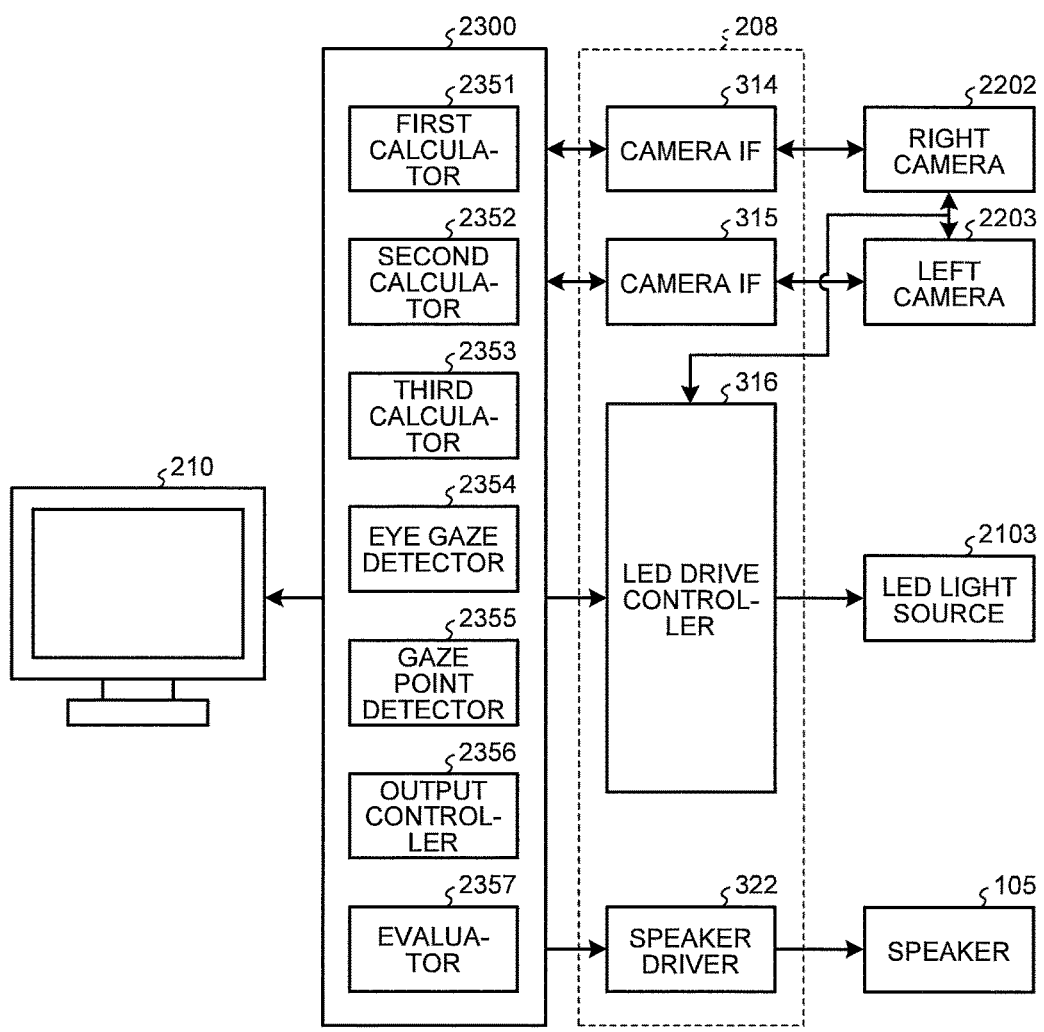
FIG. 20 is a block diagram illustrating an example of a detailed function of each unit illustrated in FIG. 19.

FIG. 20 is a block diagram illustrating an example of a detailed function of each unit illustrated in FIG. 19. The controller 2300 is connected to the display 210 and the drive/IF 208 as illustrated in FIG. 20. The drive/IF 208 includes camera IFs 314 and 315, an LED drive controller 316, and a speaker driver 322.

The right camera 2202 and the left camera 2203 are connected to the drive/IF 208 through the camera IFs 314 and 315, respectively. The subject is imaged by these cameras that are driven by the drive/IF 208.

The speaker driver 322 drives the speaker 105. The diagnosis supporting device 2100 may also include an interface (printer IF) used to be connected to a printer as a printing unit. The diagnosis supporting device 2100 may also be configured to incorporate the printer.

The controller 2300 controls the entire diagnosis supporting device 2100. The controller 2300 includes a first calculator 2351, a second calculator 2352, a third calculator 2353, an eye gaze detector 2354, a gaze point detector 2355, an output controller 2356, and an evaluator 2357. Note that the eye gaze detection apparatus need only include at least the first calculator 2351, the second calculator 2352, the third calculator 2353, and the eye gaze detector 2354.

Each element (the first calculator 2351, second calculator 2352, third calculator 2353, eye gaze detector 2354, gaze point detector 2355, output controller 2356, and evaluator 2357) included in the controller 2300 may be realized by software (program), a hardware circuit, or a combination of the software and the hardware circuit.

When realizing each unit by the program, the program is provided as a computer program product by being recorded in a computer readable recording medium such as a CD-ROM (Compact Disk Read Only Memory), a flexible disk (FD), a CD-R (Compact Disk Recordable) or a DVD (Digital Versatile Disk) in an installable or executable file format. The program may also be stored on a computer connected to a network such as the Internet and provided by being downloaded via the network. The program may also be provided or distributed via the network such as the Internet. Moreover, the program may be provided by being incorporated beforehand into the ROM or the like.

The first calculator 2351 calculates a position of the pupil center (a first position) indicating the center of the pupil from an image of the eyeball captured by the stereo camera 2102. The second calculator 2352 calculates a position of the corneal reflection center (a second position) indicating the center of the corneal reflection from the image of the eyeball being captured.

The third calculator 2353 calculates the corneal curvature center (a third position) from a straight line connecting the LED light source 2103 and the corneal reflection center. The third calculator 2353 for example calculates, as the corneal curvature center, a position which is at a distance equal to a predetermined value from the corneal reflection center on the straight line. A value determined in advance from a typical curvature radius of a cornea can be used as the predetermined value.

As the curvature radius of a cornea varies among individuals, there is a possibility of an increased error when the value determined in advance is used to calculate the corneal curvature center. The third calculator 2353 may therefore calculate the corneal curvature center while considering the variation among individuals. In this case, the third calculator 2353 first uses the pupil center and corneal reflection center calculated when causing the subject to gaze at a target position, and calculates a point of intersection (a fourth position) of a straight line connecting the pupil center and the target position and a straight line connecting the corneal reflection center and the LED light source 2103. The third calculator 2353 then calculates a distance (a first distance) between the pupil center and the calculated point of intersection and stores it into the storage 150, for example.

The target position is determined in advance and may be a position at which the three-dimensional world coordinate value can be calculated. The center position of the display screen 101 (an origin of the three-dimensional world coordinates) can be determined as the target position, for example. In this case, for example, the output controller 2356 performs control to display an image (target image) to be gazed at by the subject at the target position (center) on the display screen 101. This can cause the subject to gaze at the target position.

The target image may be any image as long as the image can be gazed at by the subject. An image with a changing display mode such as brightness and color or an image with a display mode different from that of another area can be used as the target image, for example.

Note that the target position need not be limited to the center of the display screen 101 but may be any position. A distance to an arbitrary edge of the display screen 101 is the shortest when the center thereof is determined as the target position. This allows the measurement error to be further decreased at the time of the eye gaze detection, for example.

The processing up to the calculation of the distance is executed before starting actual eye gaze detection, for example. The third calculator 2353 in the actual eye gaze detection calculates, as the corneal curvature center, a position which is at a distance equal to the distance calculated in advance from the pupil center on a straight line connecting the LED light source 2103 and the corneal reflection center.

The eye gaze detector 2354 detects the eye gaze of the subject from the pupil center and the corneal curvature center. The eye gaze detector 2354 detects a direction from the corneal curvature center toward the pupil center as an eye gaze direction of the subject, for example.

The gaze point detector 2355 detects a gaze point of the subject by using the eye gaze direction detected. The gaze point detector 2355 detects the gaze point at which the subject gazes on the display screen 101, for example. The gaze point detector 2355 detects, as the gaze point of the subject, a point of intersection of an eye gaze vector expressed in a three-dimensional world coordinate system illustrated in FIG. 18 and an XY plane, for example.

The output controller 2356 controls output of various information to the display 210 and the speaker 105. The output controller 2356 performs control to output the target image at the target position on the display 210, for example. The output controller 2356 further controls output of a diagnostic image and an evaluation result by the evaluator 2357 to the display 210.

The diagnostic image may be any image according to evaluation processing based on the result of eye gaze (gaze point) detection. When the developmental disorder is to be diagnosed, for example, there may be used a diagnostic image including an image preferred by the subject with developmental disorder (such as a geometric pattern video) and another image (such as a person video).

The evaluator 2357 performs evaluation processing based on the diagnostic image and the gaze point detected by the gaze point detector 2355. When the developmental disorder is to be diagnosed, for example, the evaluator 2357 analyzes the diagnostic image and the gaze point and evaluates whether or not the image preferred by the subject with developmental disorder is gazed at.

The output controller 2356 may display the diagnostic image similar to that of the first embodiment, while the evaluator 2357 may perform the evaluation processing similar to that performed by the evaluator 354 of the first embodiment. In other words, the eye gaze detection processing (the eye gaze detector 351) of the first embodiment may be replaced with the eye gaze detection processing (the first calculator 2351, second calculator 2352, third calculator 2353, and eye gaze detector 2354) of the second embodiment. As a result, effects of the second embodiment (such as simplification of the apparatus configuration) in addition to the effects of the first embodiment can be achieved.

Figure 21:
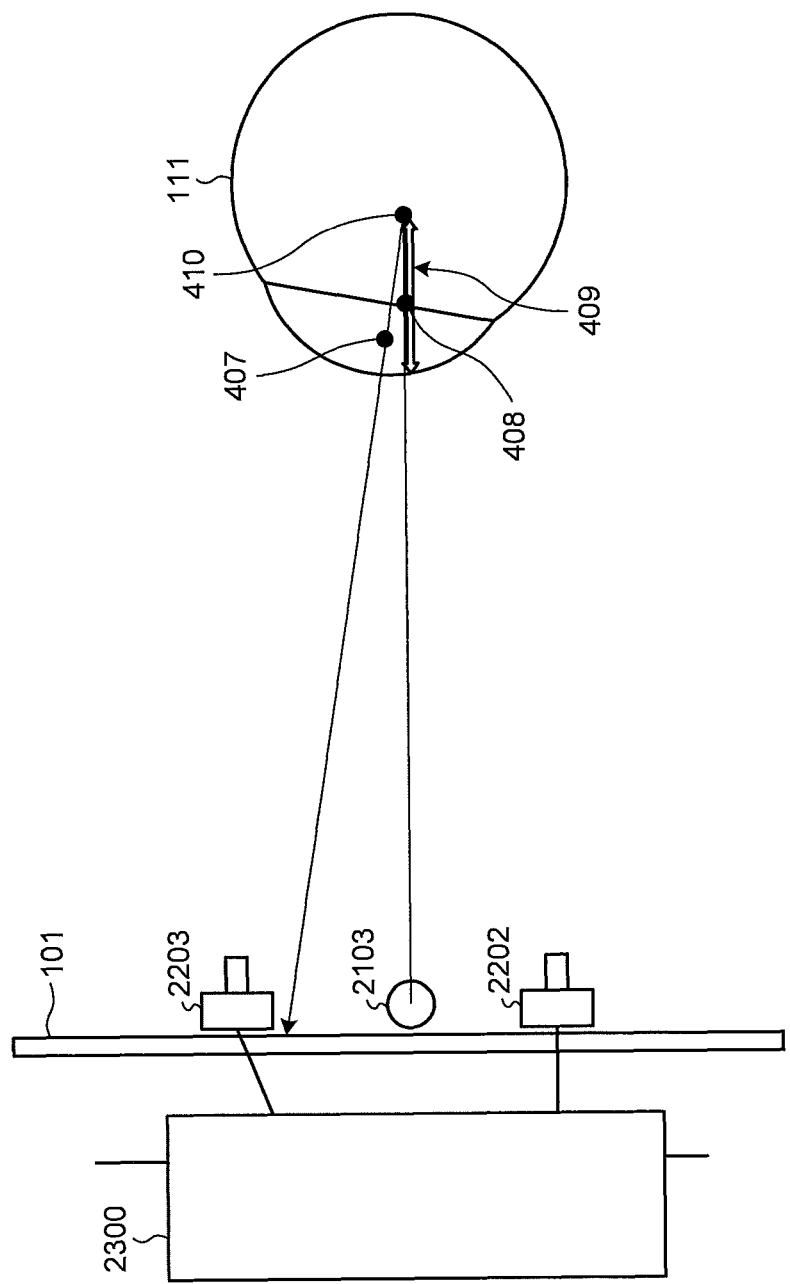
FIG. 21 is a diagram illustrating an overview of processing executed by the diagnosis supporting device according to the second embodiment.

FIG. 21 is a diagram illustrating an overview of processing executed by the diagnosis supporting device 2100 according to the present embodiment. The element described with reference to FIGS. 17 to 20 will be denoted by the same reference numeral as that in FIGS. 17 to 20 and the description of such element is omitted.

A pupil center 407 and a corneal reflection center 408 represent the center of the pupil and the center of the corneal reflection point detected when the LED light source 2103 is illuminated, respectively. A corneal curvature radius 409 represents a distance from a corneal surface to a corneal curvature center 410.

Figure 22:
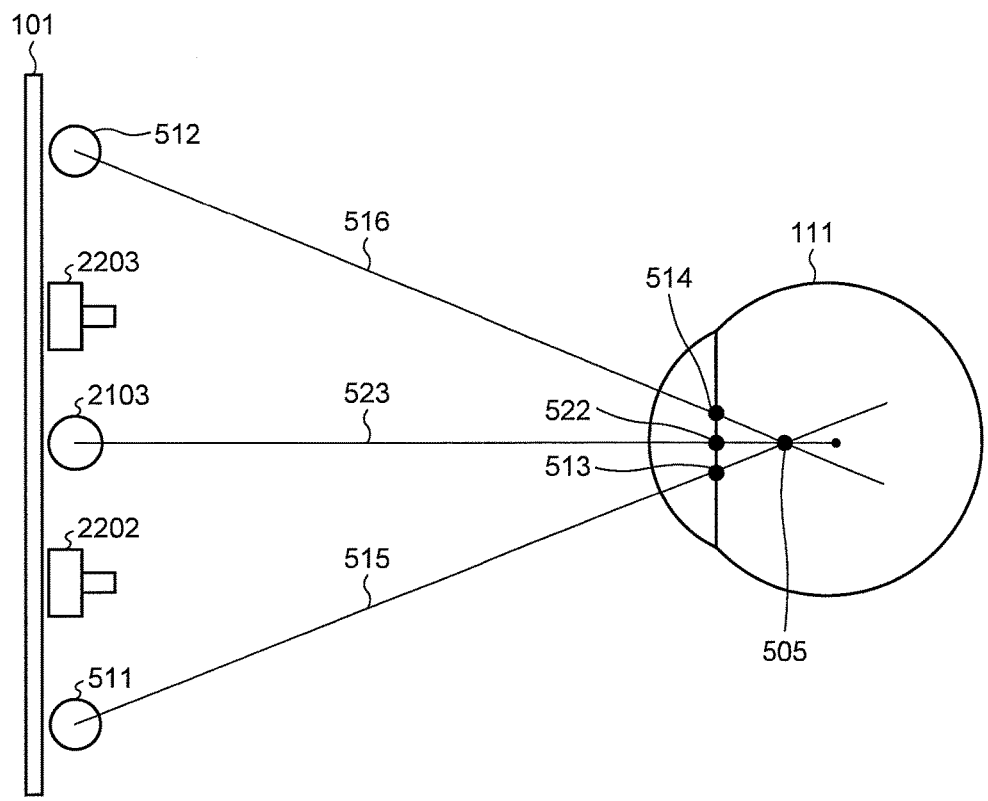
FIG. 22 is a diagram illustrating a difference between a method using two light sources and the second embodiment using one light source.

FIG. 22 is a diagram illustrating a difference between a method (hereinafter referred to as a method A) using two light sources (illuminators) and the present embodiment using one light source (illuminator). The element described with reference to FIGS. 17 to 20 will be denoted by the same reference numeral as that in FIGS. 17 to 20 and the description of such element is omitted.

The method A uses two LED light sources 511 and 512 instead of the LED light source 2103. The method A calculates a point of intersection of a straight line 515 connecting a corneal reflection center 513 and the LED light source 511 when the LED light source 511 is irradiated and a straight line 516 connecting a corneal reflection center 514 and the LED light source 512 when the LED light source 512 is irradiated. This point of intersection is a corneal curvature center 505.

On the other hand, the present embodiment considers a straight line 523 connecting a corneal reflection center 522 and the LED light source 2103 when the LED light source 2103 is irradiated. The straight line 523 passes the corneal curvature center 505. The curvature radius of a cornea is known to have little variation among individuals and have approximately a fixed value. Accordingly, the corneal curvature center when the LED light source 2103 is radiated exists on the straight line 523 and can be calculated by using a general curvature radius.

However, the position of the gaze point deviates from the original position due to the eyeball varying among individuals and cannot be detected accurately in some cases when the gaze point is calculated by using the position of the corneal curvature center that is obtained by using the general curvature radius.

Figure 23:
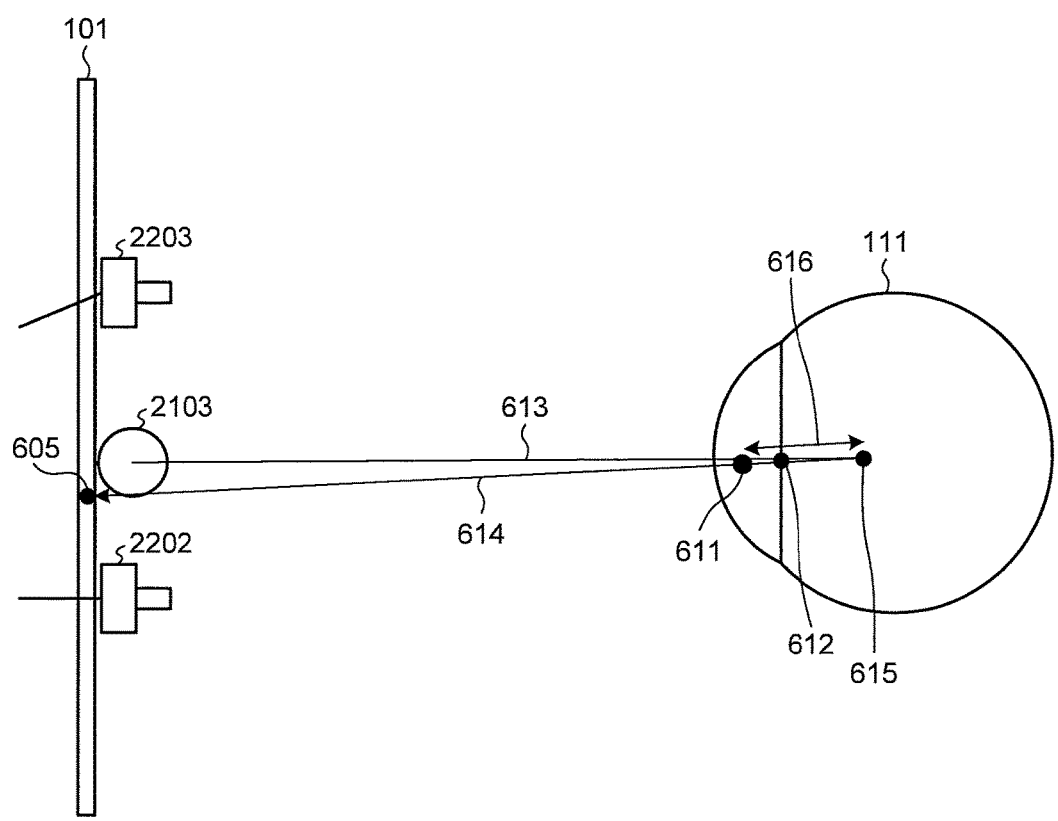
FIG. 23 is a diagram illustrating calculation processing which calculates a distance between a pupil center position and a corneal curvature center position.

FIG. 23 is a diagram illustrating calculation processing which calculates the corneal curvature center position and a distance between the pupil center position and the corneal curvature center position before performing gaze point detection (eye gaze detection). The element described with reference to FIGS. 17 to 20 will be denoted by the same reference numeral as that in FIGS. 17 to 20 and the description of such element is omitted. The connection between the left and right cameras (the right camera 2202 and left camera 2203) and the controller 2300 is omitted from the drawing.

A target position 605 is a position provided to cause the subject to gaze at a target image or the like by outputting the target image at one point on the display 210. The target position corresponds to the center of the display screen 101 in the present embodiment. A straight line 613 is a line connecting the LED light source 2103 and a corneal reflection center 612. A straight line 614 is a line connecting the target position 605 (gaze point) at which the subject gazes and a pupil center 611. A corneal curvature center 615 corresponds to a point of intersection of the straight line 613 and the straight line 614. The third calculator 2353 calculates and stores in advance a distance 616 between the pupil center 611 and the corneal curvature center 615.

Figure 24:
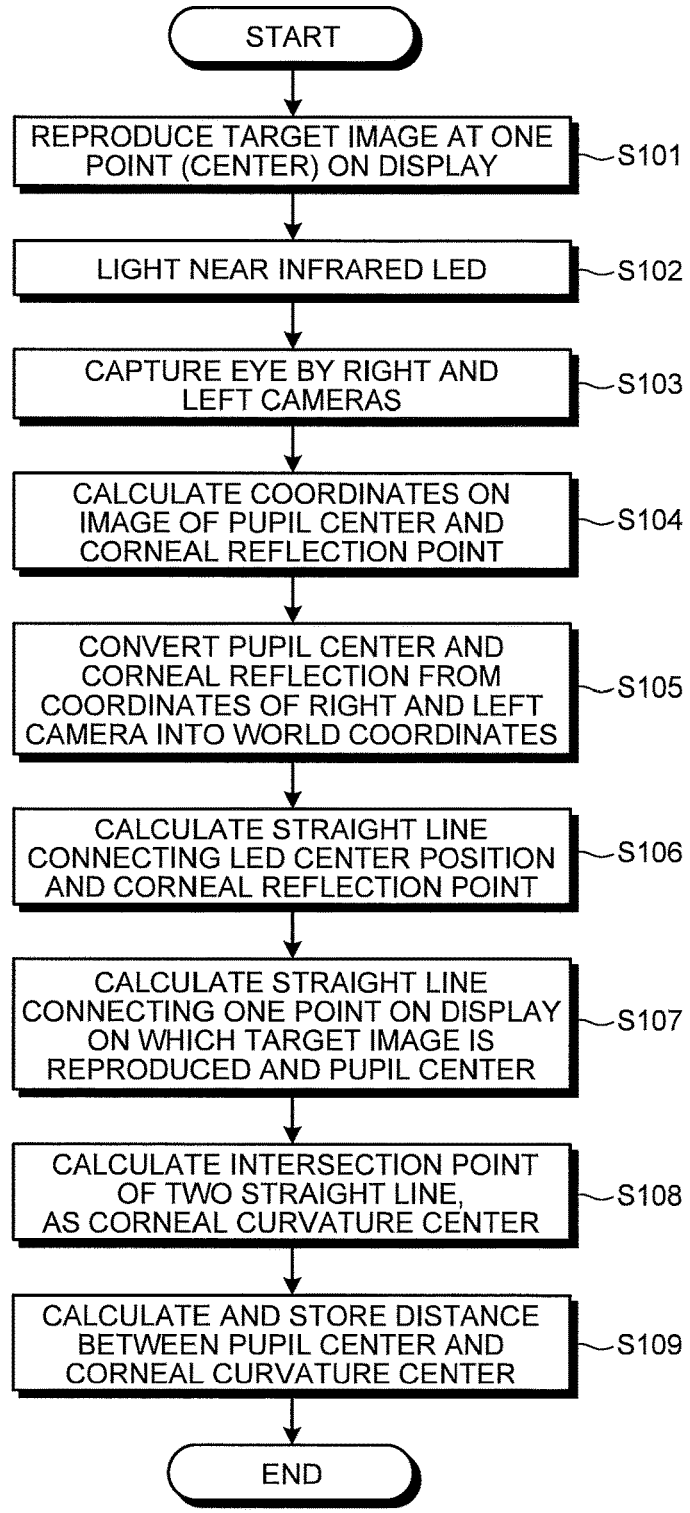
FIG. 24 is a flowchart illustrating an example of the calculation processing according to the second embodiment.

FIG. 24 is a flowchart illustrating an example of the calculation processing according to the present embodiment.

First, the output controller 2356 performs control to reproduce the target image at one point on the display screen 101 (step S101) and cause the subject to gaze at the point. The controller 2300 then uses the LED drive controller 316 to illuminate the LED light source 2103 toward the eye of the subject (step S102). The controller 2300 images the eye of the subject by using the left and right cameras (the right camera 2202 and the left camera 2203) (step S103).

The pupil is detected as a dark part (dark pupil) by the irradiation of the LED light source 2103. Moreover, the virtual image of corneal reflection is created as the reflection of the LED irradiation, where a corneal reflection point (corneal reflection center) is detected as a bright part. That is, the first calculator 2351 detects the pupil part from the captured image and calculates coordinates indicating the position of the pupil center. The second calculator 2352 detects the corneal reflection part from the captured image and calculates coordinates indicating the position of the corneal reflection center. The first calculator 2351 and the second calculator 2352 calculate the coordinate values for each of the two images obtained with the left and right cameras (step S104).

Note that a conversion parameter is calculated in advance by the camera calibration according to the stereo calibration method performed on the left and right cameras in order to obtain the three-dimensional world coordinates. The stereo calibration method can apply various conventional methods such as a method using the Tsai's camera calibration theory.

The first calculator 2351 and the second calculator 2352 use this conversion parameter and convert the coordinates of each of the pupil center and the corneal reflection center into the three-dimensional world coordinates from the coordinates of the left and right cameras (step S105). The third calculator 2353 finds a straight line connecting the world coordinates of the corneal reflection center obtained and the world coordinates of the center position of the LED light source 2103 (step S106). Next, the third calculator 2353 calculates a straight line connecting world coordinates of the center of the target image displayed at one point on the display screen 101 and the world coordinates of the pupil center (step S107). The third calculator 2353 finds a point of intersection of the straight line calculated in step S106 and the straight line calculated in step S107, and determines the point of intersection as the corneal curvature center (step S108). The third calculator 2353 calculates a distance between the pupil center and the corneal curvature center at this time and stores the distance in the storage 150 or the like (step S109). The stored distance is used to calculate the corneal curvature center when a gaze point (eye gaze) is detected in the future.

The distance between the pupil center and the corneal curvature center when the subject gazes at one point on the display 210 in the calculation processing is kept fixed within the range in which the gaze point is detected on the display 210. The distance between the pupil center and the corneal curvature center may be calculated from an average of all values calculated while the target image is reproduced or from an average of some of the values calculated while the target image is reproduced.

Figure 25:
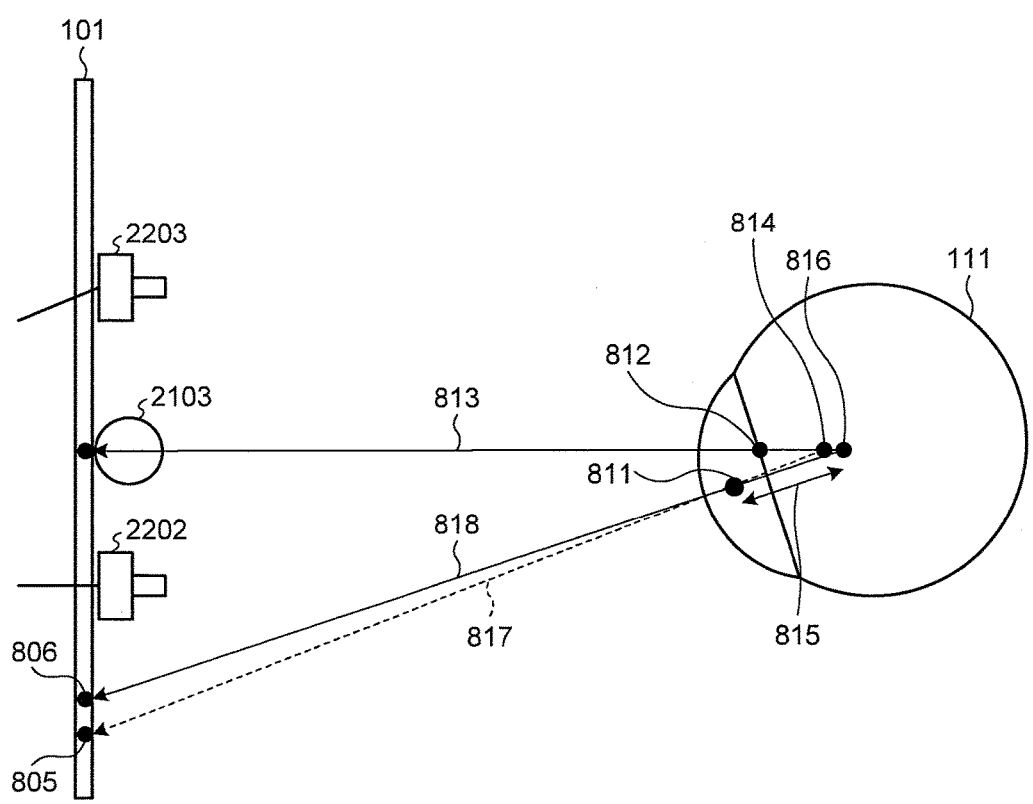
FIG. 25 is a diagram illustrating a method of calculating the corneal curvature center position by using a distance obtained in advance.

FIG. 25 is a diagram illustrating a method which uses the distance between the pupil center and the corneal curvature center obtained in advance to calculate the position of a corrected corneal curvature center when detecting the gaze point. A gaze point 805 represents a gaze point found from the corneal curvature center calculated by using a typical curvature radius. A gaze point 806 represents a gaze point found from the corneal curvature center calculated by using the distance calculated in advance.

A pupil center 811 and a corneal reflection center 812 indicate the position of the pupil center and the position of the corneal reflection center calculated when detecting the gaze point, respectively. A straight line 813 is a line connecting the LED light source 2103 and the corneal reflection center 812. A corneal curvature center 814 is the position of the corneal curvature center calculated from the typical curvature radius. A distance 815 is a distance between the pupil center and the corneal curvature center calculated in advance by the calculation processing. A corneal curvature center 816 is the position of the corneal curvature center calculated by using the distance calculated in advance. The corneal curvature center 816 is found from the corneal curvature center being present on the straight line 813 and the distance between the pupil center and the corneal curvature center being the distance 815. Accordingly, an eye gaze 817 calculated by using the typical curvature radius is corrected to an eye gaze 818. Moreover, the gaze point on the display screen 101 is corrected from the gaze point 805 to the gaze point 806. The connection between the left and right cameras (the right camera 2202 and left camera 2203) and the controller 2300 is omitted from the drawing.

Figure 26:
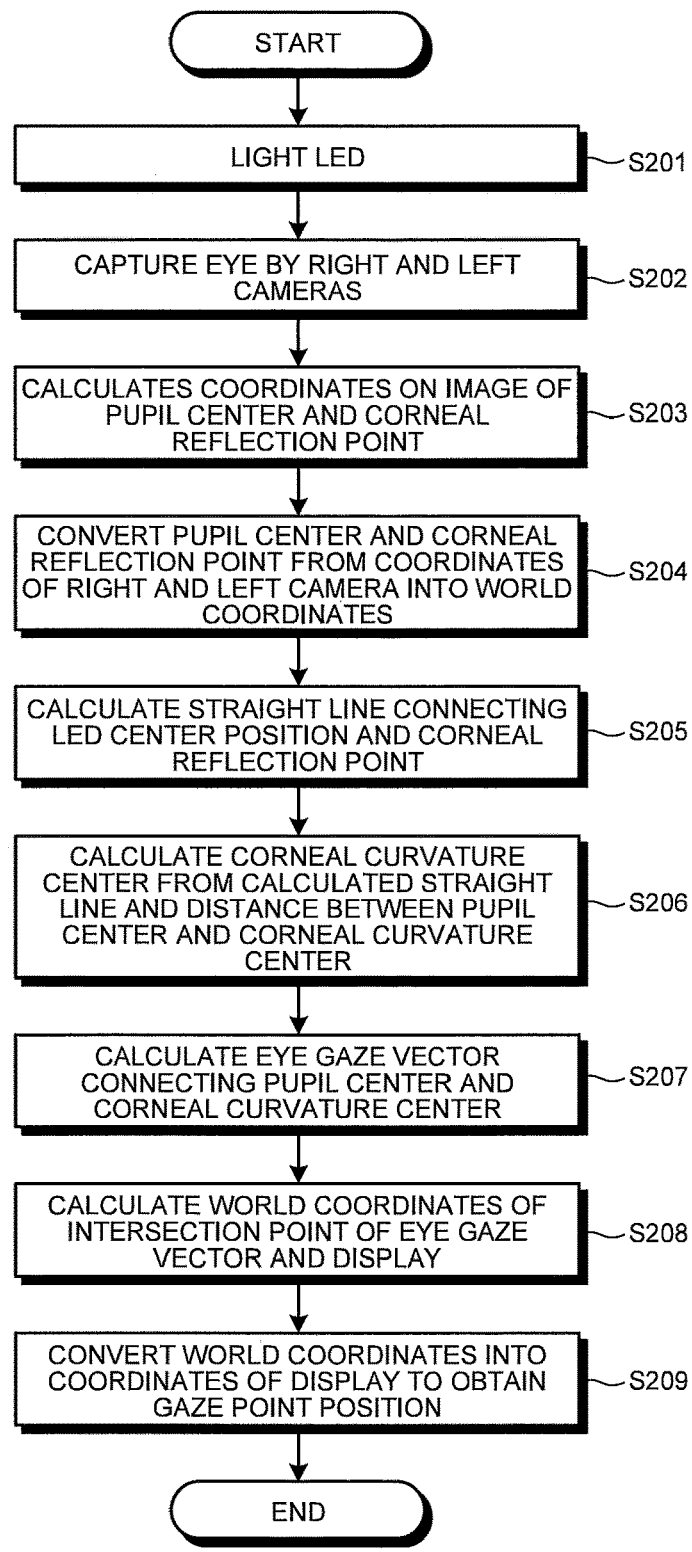
FIG. 26 is a flowchart illustrating an example of eye gaze detection processing according to the second embodiment.

FIG. 26 is a flowchart illustrating an example of eye gaze detection processing according to the present embodiment. The eye gaze detection processing illustrated in FIG. 26 can be executed as processing of detecting an eye gaze in the diagnostic processing using the diagnostic image, for example. In addition to each step illustrated in FIG. 26, the diagnostic processing includes processing of displaying the diagnostic image and evaluation processing using a detected result of the gaze point and performed by the evaluator 2357.

Steps S201 to S205 are the same as steps S102 to S106 illustrated in FIG. 24 and thus will not be described.

The third calculator 2353 calculates, as the corneal curvature center, the position which is on a straight line calculated in step S205 and is at a distance, which is equal to the distance calculated in the previous calculation processing from the pupil center (step S206).

The eye gaze detector 2354 finds a vector (eye gaze vector) connecting the pupil center and the corneal curvature center (step S207). This vector indicates the eye gaze direction of the subject. The gaze point detector 2355 calculates a three-dimensional world coordinates value of a point of intersection of the eye gaze direction and the display screen 101 (step S208). This value is a coordinates value representing in the world coordinate the one point at which the subject gazes on the display 210. The gaze point detector 2355 converts the three-dimensional world coordinates value into coordinates (x, y) represented in a two-dimensional coordinate system of the display 210 (step S209). As a result, the gaze point of the subject on the display 210 can be calculated.

The following effects can be attained according to the present embodiment, for example.

(1) The eye gaze detection can be performed by using the light source (illuminator) arranged at one place without needing to arrange the light source at two places.

(2) As the light source is arranged at one place, the apparatus can be made compact, and cost reduction is realized as well.

REFERENCE SIGNS LIST

The diagnosis supporting device and the diagnosis supporting method according to the present invention can improve the diagnostic accuracy.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A diagnosis supporting device comprising:
    an imaging unit that images a subject;
    an eye gaze detector that detects an eye gaze direction of the subject from an image imaged by the imaging unit;
    a gaze point detector that detects a gaze point of the subject in a display area of a display on the basis of the eye gaze direction; and
    an output controller that causes the display area to display a diagnostic image composed by superposing a pattern image including a geometric pattern onto a part of a natural image in which most of the display area is occupied by a person, an animal, or a plant, wherein
    at least one of hue, brightness, and chroma in the pattern image is similar to or matches hue, brightness, and chroma in a part adjacent to or slightly away from the part of the natural image.

2. The diagnosis supporting device according to claim 1, wherein the output controller causes the display to display a first diagnostic image and then a second diagnostic image in which a position of a pattern image is different from a position of a pattern image in the first diagnostic image, and
    the gaze point detector detects a gaze point of the subject when the first diagnostic image and the second diagnostic image are displayed.

3. The diagnosis supporting device according to claim 2, wherein an area of the pattern image in the first diagnostic image and an area of the pattern image in the second diagnostic image are symmetrical about a center of the display area.

4. The diagnosis supporting device according to claim 1, wherein the pattern image is continuous with an object adjacent to the part of the natural image.

5. The diagnosis supporting device according to claim 1, wherein the pattern image changes on the basis of a motion speed of the object included in the natural image.

6. The diagnosis supporting device according to claim 1, further comprising
    an evaluator determining which of the natural image and the pattern image is gazed at.

7. The diagnosis supporting device according to claim 1, further comprising:
    an illuminator which includes a light source radiating light;
    a first calculator that calculates a first position indicating a center of a pupil from an image of an eyeball of a subject, the image being captured by the imaging unit while the light being irradiated by the illuminator;
    a second calculator that calculates a second position indicating a center of corneal reflection from the image of the eyeball being captured; and
    a third calculator that calculates a third position indicating a corneal curvature center on the basis of a straight line connecting the light source and the second position,
    wherein the eye gaze detector detects an eye gaze of the subject on the basis of the first position and the third position.

8. A diagnosis supporting method comprising:
    detecting an eye gaze direction of a subject from an image captured by an imaging unit imaging the subject;
    detecting a gaze point of the subject in a display area of a display on the basis of the eye gaze direction; and
    causing the display area to display a diagnostic image composed by superposing a pattern image including a geometric pattern onto a part of a natural image in which most of the display area is occupied by a person, an animal, or a plant, wherein
    at least one of hue, brightness, and chroma in the pattern image is similar to or matches hue, brightness, and chroma in a part adjacent to or slightly away from the part of the natural image.

* * * * *